(12) United States Patent
Merritt et al.

(10) Patent No.: US 10,874,560 B2
(45) Date of Patent: Dec. 29, 2020

(54) DETECTABLE SPONGES FOR USE IN MEDICAL PROCEDURES AND METHODS OF MAKING, PACKAGING, AND ACCOUNTING FOR SAME

(71) Applicant: Covidien LP, Mansfield, MA (US)

(72) Inventors: John Merritt, San Diego, CA (US); William A. Blair, San Diego, CA (US); Tom Kane, San Diego, CA (US); John Buhler, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 630 days.

(21) Appl. No.: 15/540,331

(22) PCT Filed: Jan. 21, 2016

(86) PCT No.: PCT/US2016/014324
§ 371 (c)(1),
(2) Date: Jun. 28, 2017

(87) PCT Pub. No.: WO2016/118749
PCT Pub. Date: Jul. 28, 2016

(65) Prior Publication Data
US 2018/0333309 A1 Nov. 22, 2018

Related U.S. Application Data

(60) Provisional application No. 62/106,052, filed on Jan. 21, 2015, provisional application No. 62/138,248, (Continued)

(51) Int. Cl.
*A61F 13/44* (2006.01)
*A61B 90/98* (2016.01)
(Continued)

(52) U.S. Cl.
CPC ............. *A61F 13/44* (2013.01); *A61B 90/90* (2016.02); *A61B 90/98* (2016.02); *A61F 13/36* (2013.01);
(Continued)

(58) Field of Classification Search
CPC .......... A61F 13/44; A61F 13/36; A61B 90/90; A61B 90/98; A61B 90/39
See application file for complete search history.

(56) References Cited

U.S. PATENT DOCUMENTS 2,698,270 A * 12/1954 Mesek .................... A61F 13/44
156/177
2,740,405 A 4/1956 Riordan
(Continued)

FOREIGN PATENT DOCUMENTS

AU 199852698 B2 3/1993
AU 2003249257 A1 2/2004
(Continued)

OTHER PUBLICATIONS

Extended European Search Report, dated Jun. 12, 2018, for European Application No. 16740758.4-1113, 11 pages.
(Continued)

*Primary Examiner* — Ariana Zimbouski
(74) *Attorney, Agent, or Firm* — Carter, DeLuca & Farrell LLP

(57) ABSTRACT

Sponges suitable for use in medical procedures may include radio-opaque material, and arranged to allow individual sponges in a set, packet or package of sponges to be readily discernable using imaging technology (e.g., X-ray) to allow accurate counting of sponges. The sponges may include wireless transponders, for instance LC resonant and/or RFID transponders. Gauze or similar material is folded to enhance the ability to count the sponges. Sponges are counted and
(Continued)

banded or packaged to provide assurance that the count is accurate.

6 Claims, 8 Drawing Sheets

Related U.S. Application Data filed on Mar. 25, 2015, provisional application No. 62/164,412, filed on May 20, 2015.

(51) Int. Cl.
*A61B 90/90* (2016.01)
*A61F 13/36* (2006.01)
*A61B 90/00* (2016.01)
*A61F 13/84* (2006.01)

(52) U.S. Cl.
CPC . *A61B 2090/0805* (2016.02); *A61B 2090/376* (2016.02); *A61B 2090/3966* (2016.02); *A61F 2013/8479* (2013.01)

(56) References Cited

U.S. PATENT DOCUMENTS

| | | | |
|---|---|---|---|
| 3,031,864 A | 5/1962 | Freundlich | |
| 3,123,210 A | 3/1964 | Hermanson et al. | |
| 3,422,816 A | 1/1969 | Robinson et al. | |
| 3,587,583 A | 6/1971 | Greenberg | |
| 3,630,202 A | 12/1971 | Small | |
| D240,166 S | 6/1976 | Cartmell et al. | |
| 3,965,907 A * | 6/1976 | Hardy | A61F 13/44 |
| | | | 604/362 |
| 4,034,297 A | 7/1977 | Giorgi et al. | |
| 4,114,601 A | 9/1978 | Abels | |
| 4,193,405 A | 3/1980 | Abels | |
| D272,943 S | 3/1984 | Stone et al. | |
| 4,477,256 A | 10/1984 | Hirsch | |
| 4,540,398 A | 9/1985 | Barson et al. | |
| 4,626,251 A * | 12/1986 | Shen | A61F 13/44 |
| | | | 604/362 |
| 4,636,208 A | 1/1987 | Rath | |
| 4,639,253 A * | 1/1987 | Dyer | A61F 13/44 |
| | | | 604/362 |
| 4,645,499 A | 2/1987 | Rupinskas | |
| 4,658,818 A | 4/1987 | Miller, Jr. et al. | |
| 4,681,111 A | 7/1987 | Silvian | |
| 4,704,109 A | 11/1987 | Rupinskas | |
| 4,718,897 A | 1/1988 | Elves | |
| 4,893,118 A | 1/1990 | Lewiner et al. | |
| 4,917,694 A | 4/1990 | Jessup | |
| 4,935,019 A | 6/1990 | Papp, Jr. | |
| 4,938,901 A | 7/1990 | Groitzsch et al. | |
| 4,961,495 A | 10/1990 | Yoshida et al. | |
| 4,992,675 A | 2/1991 | Conner, Jr. et al. | |
| 5,041,103 A * | 8/1991 | Rupinskas | A61F 13/44 |
| | | | 602/900 |
| 5,045,080 A | 9/1991 | Dyer et al. | |
| 5,049,219 A | 9/1991 | Johns et al. | |
| 5,057,095 A | 10/1991 | Fabian | |
| 5,090,410 A | 2/1992 | Saper et al. | |
| 5,105,829 A | 4/1992 | Fabian et al. | |
| 5,107,862 A | 4/1992 | Fabian et al. | |
| 5,112,325 A | 5/1992 | Zachry | |
| D330,872 S | 11/1992 | Ball | |
| 5,188,126 A | 2/1993 | Fabian et al. | |
| 5,190,059 A | 3/1993 | Fabian et al. | |
| 5,203,767 A | 4/1993 | Cloyd | |
| 5,224,593 A | 7/1993 | Bennett | |
| 5,231,273 A | 7/1993 | Caswell et al. | |
| 5,235,326 A | 8/1993 | Beigel et al. | |
| 5,329,944 A | 7/1994 | Fabian et al. | |
| D353,343 S | 12/1994 | Eberhardt | |
| D354,927 S | 1/1995 | Andrau | |
| D356,052 S | 3/1995 | Andrau | |
| D359,705 S | 6/1995 | Ball | |
| 5,446,447 A | 8/1995 | Carney et al. | |
| 5,456,718 A | 10/1995 | Szymaitis | |
| 5,575,781 A | 11/1996 | DeBusk | |
| D378,614 S | 3/1997 | Jensen | |
| 5,650,596 A | 7/1997 | Morris et al. | |
| 5,664,582 A | 9/1997 | Szymaitis | |
| D385,037 S | 10/1997 | Jensen | |
| 5,725,517 A | 3/1998 | DeBusk | |
| 5,792,128 A | 8/1998 | DeBusk | |
| D412,135 S | 7/1999 | Saito | |
| 5,923,001 A | 7/1999 | Morris et al. | |
| 5,931,824 A | 8/1999 | Stewart et al. | |
| 5,963,132 A | 10/1999 | Yoakum | |
| 5,969,613 A | 10/1999 | Yeager et al. | |
| D418,773 S | 1/2000 | Saito | |
| 6,026,818 A * | 2/2000 | Blair | A61F 13/44 |
| | | | 128/899 |
| D423,673 S | 4/2000 | Bassøe | |
| 6,093,869 A | 7/2000 | Roe et al. | |
| D429,337 S | 8/2000 | Sanfilippo | |
| 6,098,800 A | 8/2000 | Bennish, Jr. et al. | |
| 6,171,985 B1 | 1/2001 | Joseph et al. | |
| 6,172,608 B1 | 1/2001 | Cole | |
| 6,201,469 B1 | 3/2001 | Balch et al. | |
| 6,211,666 B1 | 4/2001 | Acker | |
| 6,232,878 B1 | 5/2001 | Rubin | |
| 6,276,033 B1 | 8/2001 | Johnson et al. | |
| 6,317,027 B1 | 11/2001 | Watkins | |
| 6,349,234 B2 | 2/2002 | Pauly et al. | |
| 6,353,406 B1 | 3/2002 | Lanzl et al. | |
| 6,354,493 B1 | 3/2002 | Mon | |
| 6,359,562 B2 | 3/2002 | Rubin | |
| 6,366,206 B1 | 4/2002 | Ishikawa et al. | |
| D456,907 S | 5/2002 | Sanfilippo | |
| D457,634 S | 5/2002 | Rouns et al. | |
| 6,384,296 B1 | 5/2002 | Roe et al. | |
| 6,401,722 B1 | 6/2002 | Krag | |
| 6,441,741 B1 | 8/2002 | Yoakum | |
| D471,281 S | 3/2003 | Baura et al. | |
| 6,557,752 B1 | 5/2003 | Yacoob | |
| 6,566,997 B1 | 5/2003 | Bradin | |
| 6,588,661 B2 | 7/2003 | Degrauwe et al. | |
| 6,632,216 B2 | 10/2003 | Houzego et al. | |
| 6,641,039 B2 | 11/2003 | Southard | |
| 6,648,223 B2 | 11/2003 | Boukhny et al. | |
| 6,650,143 B1 | 11/2003 | Peng | |
| 6,650,240 B2 | 11/2003 | Lee et al. | |
| 6,667,902 B2 | 12/2003 | Peng | |
| 6,671,040 B2 | 12/2003 | Fong et al. | |
| 6,696,954 B2 | 2/2004 | Chung | |
| 6,700,151 B2 | 3/2004 | Peng | |
| 6,734,795 B2 | 5/2004 | Price | |
| 6,749,554 B1 | 6/2004 | Snow et al. | |
| 6,753,783 B2 | 6/2004 | Friedman et al. | |
| 6,766,960 B2 | 7/2004 | Peng | |
| D495,055 S | 8/2004 | Silber | |
| 6,774,800 B2 | 8/2004 | Friedman et al. | |
| 6,777,623 B2 | 8/2004 | Ballard | |
| 6,777,757 B2 | 8/2004 | Peng et al. | |
| 6,778,089 B2 | 8/2004 | Yoakum | |
| 6,786,405 B2 | 9/2004 | Wiedenhoefer | |
| 6,791,891 B1 | 9/2004 | Peng et al. | |
| 6,798,693 B2 | 9/2004 | Peng | |
| 6,812,824 B1 | 11/2004 | Goldinger et al. | |
| 6,812,842 B2 | 11/2004 | Dimmer | |
| 6,822,570 B2 | 11/2004 | Dimmer et al. | |
| 6,822,888 B2 | 11/2004 | Peng | |
| 6,838,990 B2 | 1/2005 | Dimmer | |
| 6,856,540 B2 | 2/2005 | Peng et al. | |
| D502,419 S | 3/2005 | Copen | |
| 6,861,639 B2 | 3/2005 | Al-Ali | |
| 6,861,954 B2 | 3/2005 | Levin | |
| 6,875,199 B2 | 4/2005 | Altman | |
| 6,879,300 B2 | 4/2005 | Rochelle et al. | |
| 6,898,116 B2 | 5/2005 | Peng | |
| 6,909,366 B1 | 6/2005 | Marsh et al. | |
| 6,940,751 B2 | 9/2005 | Peng et al. | |

(56) References Cited

U.S. PATENT DOCUMENTS

| | | |
|---|---|---|
| D511,004 S | 10/2005 | Masuda |
| 6,951,305 B2 | 10/2005 | Overhultz et al. |
| 6,956,258 B2 | 10/2005 | Peng |
| D511,384 S | 11/2005 | Masuda |
| 6,972,986 B2 | 12/2005 | Peng et al. |
| 6,977,504 B2 | 12/2005 | Wright et al. |
| 6,992,925 B2 | 1/2006 | Peng |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,031,209 B2 | 4/2006 | Wang et al. |
| 7,037,336 B2 | 5/2006 | Ward |
| 7,042,722 B2 | 5/2006 | Suzuki et al. |
| D526,586 S | 8/2006 | McCaghren et al. |
| 7,098,793 B2 | 8/2006 | Chung |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,160,258 B2 | 1/2007 | Imran et al. |
| D536,673 S | 2/2007 | Silber |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,227,469 B2 | 6/2007 | Varner et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,269,047 B1 | 9/2007 | Fong et al. |
| 7,299,981 B2 | 11/2007 | Hickle et al. |
| D557,423 S | 12/2007 | Chen |
| D558,352 S | 12/2007 | Sanfilippo |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| 7,471,541 B2 | 12/2008 | Fong et al. |
| D584,414 S | 1/2009 | Lash et al. |
| 7,474,222 B2 | 1/2009 | Yang et al. |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| D590,342 S | 4/2009 | Dávila et al. |
| 7,513,425 B2 | 4/2009 | Chung |
| 7,541,933 B2 | 6/2009 | Volpi et al. |
| 7,557,710 B2 | 7/2009 | Sanchez et al. |
| D598,110 S | 8/2009 | Phillips et al. |
| D598,114 S | 8/2009 | Cryan |
| 7,596,850 B2 | 10/2009 | Barth et al. |
| 7,609,538 B1 | 10/2009 | Lee et al. |
| 7,644,016 B2 | 1/2010 | Nycz et al. |
| 7,696,877 B2 | 4/2010 | Barnes et al. |
| 7,703,674 B2 | 4/2010 | Stewart et al. |
| 7,769,422 B2 | 8/2010 | DiSilvestro et al. |
| 7,795,491 B2 | 9/2010 | Stewart et al. |
| 7,816,003 B1 | 10/2010 | Luchio |
| 7,837,694 B2 | 11/2010 | Tethrake et al. |
| 7,855,656 B2 | 12/2010 | Maschke |
| 7,876,097 B2 | 1/2011 | Greim |
| 7,898,420 B2 | 3/2011 | Blair et al. |
| 8,072,310 B1 | 12/2011 | Everhart |
| 8,082,192 B2 | 12/2011 | Nycz et al. |
| 8,105,296 B2 | 1/2012 | Morris et al. |
| 8,181,860 B2 | 5/2012 | Fleck et al. |
| 8,193,938 B2 | 6/2012 | Halberthal et al. |
| 8,256,674 B2 | 9/2012 | Fleck et al. |
| 8,259,518 B2 | 9/2012 | Peng et al. |
| 8,279,068 B2 | 10/2012 | Morris et al. |
| 8,358,212 B2 | 1/2013 | Blair |
| 8,454,613 B2 | 6/2013 | Tethrake et al. |
| 8,477,076 B1 | 7/2013 | Nero, Jr. et al. |
| 8,479,989 B2 | 7/2013 | Fleck et al. |
| 8,576,076 B2 | 11/2013 | Morris et al. |
| 8,624,721 B2 | 1/2014 | Barker, Jr. et al. |
| 8,710,957 B2 | 4/2014 | Blair et al. |
| 8,726,911 B2 | 5/2014 | Blair |
| 8,780,660 B2 | 7/2014 | Peng |
| 8,797,820 B2 | 8/2014 | Peng et al. |
| 8,872,662 B2 | 10/2014 | Halberthal et al. |
| 8,878,668 B2 | 11/2014 | Blair et al. |
| 8,978,229 B2 | 3/2015 | Halberthal et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,089,366 B2 | 7/2015 | Garner-Richards et al. |
| 9,119,667 B2 | 9/2015 | Halberthal et al. |
| 9,168,104 B2 | 10/2015 | Dein |
| 9,414,973 B2 | 8/2016 | Fleck et al. |
| 9,507,981 B2 | 11/2016 | Dor et al. |
| 9,530,036 B2 | 12/2016 | Fleck et al. |
| 9,672,397 B2 | 6/2017 | Fleck et al. |
| 9,717,565 B2 | 8/2017 | Blair |
| 9,730,850 B2 | 8/2017 | Blair et al. |
| 9,814,540 B2 | 11/2017 | Blair et al. |
| 2001/0000659 A1 | 5/2001 | Hayashi et al. |
| 2001/0030610 A1 | 10/2001 | Rochelle et al. |
| 2002/0011932 A1 | 1/2002 | Rodgers et al. |
| 2002/0032435 A1 | 3/2002 | Levin |
| 2002/0070863 A1 | 6/2002 | Brooking |
| 2002/0143320 A1 | 10/2002 | Levin |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2003/0111592 A1 | 6/2003 | Al-Ali |
| 2004/0008123 A1 | 1/2004 | Carrender et al. |
| 2004/0129279 A1 | 7/2004 | Fabian et al. |
| 2004/0137844 A1 | 7/2004 | Desjeux et al. |
| 2004/0138554 A1 | 7/2004 | Dimmer et al. |
| 2004/0250819 A1 | 12/2004 | Blair et al. |
| 2005/0049564 A1 | 3/2005 | Fabian |
| 2005/0110640 A1 | 5/2005 | Chung |
| 2005/0131397 A1 | 6/2005 | Levin |
| 2005/0154293 A1 | 7/2005 | Gisselberg et al. |
| 2005/0203470 A1 | 9/2005 | Ballard |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0054107 A1 | 3/2006 | Baker |
| 2006/0084934 A1 | 4/2006 | Frank |
| 2006/0106368 A1 | 5/2006 | Miller et al. |
| 2006/0187044 A1 | 8/2006 | Fabian et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2006/0270933 A1 | 11/2006 | Benson et al. |
| 2007/0000605 A1 | 1/2007 | Millette et al. |
| 2007/0034670 A1 | 2/2007 | Racenet et al. |
| 2007/0038233 A1 | 2/2007 | Martinez et al. |
| 2007/0051473 A1 | 3/2007 | Speich |

(56) References Cited

U.S. PATENT DOCUMENTS

| | | |
|---|---|---|
| 2007/0055109 A1 | 3/2007 | Bass et al. |
| 2007/0069866 A1 | 3/2007 | Schuessler et al. |
| 2007/0075176 A1 | 4/2007 | Andrews et al. |
| 2007/0109099 A1 | 5/2007 | Raphaeli et al. |
| 2007/0112649 A1 | 5/2007 | Schlabach |
| 2007/0125392 A1 | 6/2007 | Olson, Jr. et al. |
| 2007/0152823 A1 | 7/2007 | Hirahara et al. |
| 2007/0160494 A1 | 7/2007 | Sands |
| 2007/0209957 A1 | 9/2007 | Glenn et al. |
| 2007/0216062 A1 | 9/2007 | Frank |
| 2007/0216526 A1 | 9/2007 | Volpi et al. |
| 2007/0219516 A1 | 9/2007 | Patel et al. |
| 2007/0238982 A1 | 10/2007 | Caylor, III |
| 2007/0239289 A1 | 10/2007 | Cambre et al. |
| 2007/0265690 A1 | 11/2007 | Lichtenstein et al. |
| 2007/0270660 A1 | 11/2007 | Caylor, III et al. |
| 2007/0281153 A1 | 12/2007 | Yamamoto |
| 2008/0001760 A1 | 1/2008 | Oh et al. |
| 2008/0007411 A1 | 1/2008 | Levin |
| 2008/0018432 A1 | 1/2008 | Volpi et al. |
| 2008/0020189 A1 | 1/2008 | Hofmair et al. |
| 2008/0021308 A1 | 1/2008 | Dimmer et al. |
| 2008/0024277 A1 | 1/2008 | Volpi et al. |
| 2008/0051746 A1 | 2/2008 | Shen-Gunther |
| 2008/0086771 A1 | 4/2008 | Li et al. |
| 2008/0132860 A1 | 6/2008 | Smith et al. |
| 2008/0231452 A1 | 9/2008 | Levin |
| 2008/0275327 A1 | 11/2008 | Faarbaek et al. |
| 2008/0281190 A1 | 11/2008 | Petcavich et al. |
| 2008/0296373 A1 | 12/2008 | Zmood et al. |
| 2009/0008449 A1 | 1/2009 | Qing et al. |
| 2009/0051485 A1 | 2/2009 | Corry et al. |
| 2009/0267765 A1 | 10/2009 | Greene et al. |
| 2009/0315681 A1* | 12/2009 | Blair ............... A61B 5/06 340/10.1 |
| 2009/0322485 A1 | 12/2009 | Barnes et al. |
| 2010/0033309 A1 | 2/2010 | Blair |
| 2010/0108079 A1* | 5/2010 | Blair ............... G06K 19/04 128/899 |
| 2010/0109848 A1 | 5/2010 | Blair et al. |
| 2010/0179822 A1 | 7/2010 | Reppas |
| 2010/0259393 A1 | 10/2010 | Marur et al. |
| 2011/0181394 A1 | 7/2011 | Blair |
| 2012/0031547 A1 | 2/2012 | Halberthal et al. |
| 2012/0065566 A1* | 3/2012 | Bar-Natan ........ A61F 13/00085 602/53 |
| 2012/0116499 A1 | 5/2012 | Goetzen et al. |
| 2013/0088354 A1 | 4/2013 | Thomas |
| 2013/0199720 A1 | 8/2013 | Halberthal et al. |
| 2014/0243770 A1* | 8/2014 | Stewart ............ A61F 13/44 604/362 |
| 2014/0303580 A1 | 10/2014 | Blair |
| 2015/0216610 A1 | 8/2015 | Augustine |
| 2015/0272688 A1 | 10/2015 | Blair et al. |
| 2015/0317555 A1 | 11/2015 | Dor et al. |
| 2015/0320506 A1 | 11/2015 | Sayles |
| 2016/0070942 A1 | 3/2016 | Dor et al. |
| 2016/0135895 A1 | 5/2016 | Faasse et al. |
| 2016/0157957 A1 | 6/2016 | Blair |
| 2016/0210548 A1 | 7/2016 | Blair |
| 2016/0212577 A1 | 7/2016 | Dor et al. |
| 2016/0250000 A1 | 9/2016 | Blair |
| 2017/0027660 A1 | 2/2017 | Blair |
| 2017/0296301 A1 | 10/2017 | Dor et al. |
| 2017/0348172 A1 | 12/2017 | Blair et al. |
| 2018/0000555 A1 | 1/2018 | Blair |
| 2018/0000556 A1 | 1/2018 | Blair |

FOREIGN PATENT DOCUMENTS

| | | |
|---|---|---|
| CA | 1 171 260 A | 7/1984 |
| CN | 101460096 A | 6/2009 |
| CN | 2009/151946 A1 | 12/2009 |
| CN | 101896131 A | 11/2010 |
| EP | 1 612 554 A1 | 1/2006 |
| EP | 2 087 850 A2 | 8/2009 |
| JP | 2009539478 A | 11/2009 |
| WO | 86/02539 A1 | 5/1986 |
| WO | 02/39917 A1 | 5/2002 |
| WO | 03/073934 A1 | 9/2003 |
| WO | 2004/008387 A1 | 1/2004 |
| WO | 2004054801 A1 | 7/2004 |
| WO | 2004/086997 A1 | 10/2004 |
| WO | 2006/060781 A1 | 6/2006 |
| WO | 2007/120736 A2 | 10/2007 |
| WO | 2007/146091 A1 | 12/2007 |
| WO | 2008/008449 A2 | 1/2008 |
| WO | 2008/024921 A1 | 2/2008 |
| WO | 2008/106552 A1 | 9/2008 |
| WO | 2008/112709 A1 | 9/2008 |
| WO | 2008/133634 A1 | 11/2008 |
| WO | 2009/154987 A1 | 12/2009 |
| WO | 2010/134826 A1 | 11/2010 |

OTHER PUBLICATIONS

International Search Report for (PCT/US2016/014324) date of completion is Apr. 18, 2016 (5 pages).
Chinese First Office Action dated Jul. 3, 2019 corresponding to counterpart Patent Application CN 201610035445.2.
Chinese Search Report dated Jun. 25, 2019 corresponding to counterpart Patent Application CN 201610035445.2.
Bacheldor, "Surgical Sponges Get Smart," *RFID Journal*, Jul. 26, 2006, 2 pages.
Barnes et al., "Method, Apparatus and Article for Detection of Transponder Tagged Objects, for Example During Surgery," U.S. Appl. No. 61/056,787, filed May 28, 2008, 60 pages.
Barnes et al., "Method, Apparatus and Article for Detection of Transponder Tagged Objects, for Example During Surgery," U.S. Appl. No. 61/091,667, filed Aug. 25, 2008, 76 pages.
Blair et al., "Apparatus and Method for Detecting Objects Using Tags and Wideband Detection Device," U.S. Appl. No. 60/811,376, filed Jun. 6, 2006.
Blair et al., "Method and Apparatus to Detect Transponder Tagged Objects and to Communicate with Medical Telemetry Devices, for Example During Medical Procedures," U.S. Appl. No. 61/242,699, filed Sep. 15, 2009, 158 pages.
Blair et al., "Method and Apparatus to Detect Transponder Tagged Objects and to Communicate with Medical Telemetry Devices, for Example During Surgery," U.S. Appl. No. 61/222,847, filed Jul. 2, 2009, 122 pages.
Blair et al., "Method and Apparatus to Detect Transponder Tagged Objects, for Example During Medical Procedures," U.S. Appl. No. 61/242,704, filed Sep. 15, 2009, 127 pages.
Blair et al., "Method and Apparatus to Detect Transponder Tagged Objects, for Example During Surgery," U.S. Appl. No. 61/109,104, filed Oct. 28, 2008, 73 pages.
Blair et al., "Method and Apparatus to Detect Transponder Tagged Objects, for Example During Surgery," U.S. Appl. No. 61/222,443, filed Jul. 1, 2009, 95 pages.
Blair et al., "Method, Apparatus and Article for Detection of Transponder Tagged Objects, for Example During Surgery," U.S. Appl. No. 60/892,208, filed Feb. 28, 2007, 50 pages.
Blair et al., "Tag and Detection Device," U.S. Appl. No. 60/458,222, filed Mar. 27, 2003, 23 pages.
Blair et al., "Transponder Housing and Device to Mark Implements, Such As Surgical Implements, and Method of Using Same," U.S. Appl. No. 60/894,435, filed Mar. 12, 2007, 30 pages.
Blair, "Apparatus, Method, and Article for Detection and Identification of Multi-Mode Integral Transponder Tagged Objects," U.S. Appl. No. 61/056,229, filed May 27, 2008, 38 pages.
Blair, "Apparatuses to Physically Couple Transponder to Objects, Such As Surgical Objects, and Methods of Using Same," U.S. Appl. No. 62/121,358, filed Feb. 26, 2015, 88 pages.
Blair, "Article to Attach a Transponder to a Surgical Sponge," Design U.S. Appl. No. 29/336,009, filed Apr. 27, 2009, 4 pages.

(56) References Cited

OTHER PUBLICATIONS

Blair, "Attachment Article to Attach a Transponder to a Surgical Sponge," Design U.S. Appl. No. 29/336,009, filed Apr. 27, 2009, 4 pages.

Blair, "Attachment Article to Attach a Transponder to a Surgical Sponge," Design U.S. Appl. No. 29/336,008, filed Apr. 27, 2009, 7 pages.

Blair, "Detectable Surgical Objects and Methods of Making Same," U.S. Appl. No. 61/109,142, filed Oct. 28, 2008, 47 pages.

Blair, "Method and Apparatus to Account for Transponder Tagged Objects Used During Medical Procedures," U.S. Appl. No. 61/263,726, filed Nov. 23, 2009, 78 pages.

Blair, "Multi-Modal Transponder and Method and Apparatus to Detect Same," U.S. Appl. No. 61/102,749, filed Oct. 3, 2008, 48 pages.

Blair, "Radio Opaque Device with Resonant Nanostructures," U.S. Appl. No. 61/163,813, filed Mar. 26, 2009, 47 pages.

Blair, "Transponder Device to Mark Implements, Such as Surgical Implements, and Method of Manufacturing and Using Same," U.S. Appl. No. 61/086,727, filed Aug. 6, 2008, 30 pages.

Blair, "Transponder Device to Mark Implements, Such as Surgical Implements, and Method of Manufacturing and Using Same," U.S. Appl. No. 61/220,452, filed Jun. 25, 2009, 46 pages.

Blair, "Transponder Device to Mark Implements, Such as Surgical Implements, and Method of Manufacturing and Using Same," U.S. Appl. No. 61/224,323, filed Jul. 9, 2009, 57 pages.

Blair, "Transponder Housing," Design U.S. Appl. No. 29/322,539, filed Aug. 6, 2008, 6 pages.

Clearcount Medical Solutions, "The SmartSponge System," Downloaded Oct. 20, 2009.

Extended European Search Report, dated Jul. 30, 2015, for European Application No. 14176398.7, 7 pages.

Haldor Advanced Technologies, "Haldor Advanced Technologies Releases a Breakthrough New Sponge Management Solution: Modular, Mobile, Wireless, and Tailored per Use-case and Requirements," Sep. 8, 2015, retrieved from http://ww1.prweb.com/prfiles/2015/09/06/12938762/ORLocate%205Sponge%20Solution-September%202015.pdf, 2 pages.

International Search Report, dated Dec. 23, 2014, for PCT/US2014/045942, 3 pages.

International Search Report, dated May 13, 2016, for International Application No. PCT/US2016/014335, 3 pages.

Macario, et al., "Initial Clinical Evaluation of a Handheld Device for Detecting Retained Surgical Gauze Sponges Using Radiofrequency Identification Technology," Arch. Surg., vol. 14, Jul. 2005, pp. 659-662.

Technologies Solutions Group, "ORtrack," 2013, 2 pages.

Technologies Solutions Group, "Sponge-Track," 2013, 2 pages.

Written Opinion, dated Dec. 23, 2014, for PCT/US2014/045942, 7 pages.

Written Opinion, dated May 2, 2016, for International Application No. PCT/US2016/014324, 13 pages.

Australian Examination Report No. 1 dated Aug. 7, 2019 corresponding to counterpart Patent Application AU 2016200113.

Chinese Office Action for application No. 201680006406.8 dated Apr. 16, 2020 with English translation.

* cited by examiner

DETECTABLE SPONGES FOR USE IN MEDICAL PROCEDURES AND METHODS OF MAKING, PACKAGING, AND ACCOUNTING FOR SAME

CROSS-REFERENCE TO RELATED APPLICATIONS

This application is a U.S. national stage application filed under 35 U.S.C. § 371 of International Patent Application PCT/US2016/014324, accorded an international filing date of Jan. 21, 2016, which claims the benefit of U.S. Provisional Patent Application Nos. 62/106,052 filed Jan. 21, 2015; 62/138,248 filed Mar. 25, 2015; and 62/164,412 filed May 20, 2015, which applications are incorporated herein by reference in their entirety.

BACKGROUND

Technical Field

The present disclosure generally relates to sponges (e.g., gauze) suitable for use in medical procedures, which may include radio-opaque markers and optionally wireless transponders.

Description of the Related Art

Sponges of a variety of forms have long been a staple article used in performing medical procedures, for instance surgeries, labor and deliver (L&D), emergency room (ER) procedures, and even general clinical procedures. Medical care providers (e.g., physicians, nurses, dentists, orderlies) typically use sponges to soak up blood and other bodily fluids, to apply pressure, or to fill cavities in bodily organs or structures.

Sponges typically comprise gauze, folded into several layers. Sponges often resemble multi-layer rectangular pads, although other may come in other shapes. The gauze is typically sterile prior to use, and may or may not be received in sterile packaging. Sponges typically employ a lint free material, to prevent leaving stray portions behind during a medical procedure.

Unintentional foreign body retention is a concern during many medical procedures, particularly during surgical or L&D procedures. Medical care providers may employ sponges in various cavities in the body during the procedure. The sponges can be difficult to visually locate in the body, particularly after absorbing fluids such as blood. If left in the body, a sponge may be a source of infection or may give rise to other complications. Such can cause adverse heath consequence, requiring further medical procedures, and even lead to long term illness or even death.

In an effort to prevent unintentional retention of sponges, some hospitals have instituted procedures which include checklists or require multiple counts to be performed to track the use and return of objects during surgery. Such manual approaches are inefficient, requiring the time of highly trained personnel, and are prone to error.

In an effort to further prevent unintentional retention of sponges, many sponges are marked or tagged with radio-opaque material. Radio-opaque material tends to absorb electromagnetic energy in the X-ray or even Gamma ray ranges of frequencies, causing such material to be visually apparent via X-ray medical imaging.

As a further effort to prevent unintentional retention of sponges, some sponges are marked or tagged with wireless transponders. These wireless transponders are typically of one of two types: i) LC resonant transponder, or ii) radio-frequency identification (RFID) transponders.

LC resonant transponders are typically very simple circuits, comprising an inductor and a capacitor which resonate at some defined frequencies, hence the name LC resonant transponder. The LC resonant transponder returns a wireless response signal at or proximate a defined frequency in response to being subjected to wireless interrogation signal at or proximate a defined frequency (e.g., pulsed wideband wireless signals). Depending on the LC resonant transponder, the wireless response signal may be at the same or at a different frequency than the interrogation signal. The LC resonant transponder does not store or provide any unique identification information or identifier. Thus, the LC resonant transponder serves as a simple presence/absence transponder, similar in some respects to Electronic Article Surveillance (EAS) transponders or tags commonly encounters on retail goods in retail stores.

RFID transponders typically take the form of a passive RFID transponder, that is one that derives power from an interrogation signal rather than from an on-board battery. RFID transponders are typically more complicated than LC resonant transponders. For example, passive RFID transponders have power circuitry which converts an RF or microwave signal into DC power, and a storage device (e.g., capacitor) for temporarily storing power to power the passive RFID transponder when being interrogated. RFID transponders typically have one or more memories, at least one of which stores a unique identifier. The unique identifier is encoded in a response signal which the RFID transponder returns in response to an interrogation signal. Some RFID transponders have memory that cannot only be read, but can also be written to more than once. Some RFID transponders have logic circuits, and may recognize commands, and even be able to recognize commands that are addressed to the specific RFID transponder. While denominated as "radio frequency identification" RFID transponders typically operate in either the radio or the microwave frequency bands of the electromagnetic spectrum.

LC transponders have been successfully used to determine the presence or absence of sponges in the body during medical procedures. Examples of such an approach are discussed in U.S. Pat. No. 6,026,818, issued Feb. 22, 2000, and U.S. Patent Publication No. US 2004/0250819, published Dec. 16, 2004.

In contrast, RFID transponders are typically used in a count-in/count-out process during medical procedures. The count-in/count-out process typically requires taking an inventory of all RFID transponder tagged objects before or at the start of a medical procedure, then taking an inventory of all RFID transponder tagged objects after or at the end of the medical procedure, and comparing the inventories.

BRIEF SUMMARY

Producing sponges typically employs many automated operations and/or manual operations. Strips of gauze may be cut into defined lengths, and folded into sponges. The gauze may include one or more radio-opaque makers. The radio-opaque markers may be woven into the gauze, for instance during the manufacturing of the gauze itself, or following manufacturing of the gauze. Alternatively, or additionally, radio-opaque markers may be applied, fixed or otherwise attached the gauze after manufacture of the gauze.

The gauze may additionally, or alternatively, include one or more wireless transponders. The wireless transponders may take any of a variety of forms, for example LC resonant transponders or RFID transponders, or both. Notably, LC resonant transponders may operate at relatively lower frequencies as compared to the frequencies typical of passive RFID transponders. This provides greater range when the transponder is in bodily tissue, enhancing detectability in the body. The wireless transponders may be applied, fixed or otherwise attached to the gauze, typically before being folding.

The wireless transponder(s) may, for example, be encased in a closed pouch, before being attached to the gauze, for example via sewing or stitching, or via heat sealing or welding for instance RF heat welding. In some implementations, the pouch may take the form of laminate, for instance a pouch of thermoplastic polyurethane (TPU), nylon and/or or polyvinyl chloride (PVC) impregnated fabric.

Alternatively, the wireless transponder(s) may, for example, be encased between the piece of gauze and another piece of material, The other piece of material may take the form of a textile, for example a woven or knitted textile. Alternatively, the other piece of material may take the form of a membrane, for example a polymer membrane, for instance a membrane of thermoplastic polyurethane (TPU), nylon or polyvinyl chloride (PVC) impregnated fabric. In some implementations, the other piece of material may take the form of laminate. The other piece of material may be attached to the gauze, for example via sewing or stitching, or via heat sealing or welding for instance RF heat welding, trapping the wireless transponder between the piece of gauze and the other piece of material.

As a further alternative, the wires transponder may be directly applied, fixed or otherwise attached to the gauze, for example via a bio-compatible adhesive, bio-compatible epoxy or encapsulant, or via heat sealing or RF welding.

Sets of sponges may be packaged together in packets. For example, a set of five sponges may be packaged together. An imaging system may image the set of sponges to assure that each set, packet or package contains a set number of sponges. For example, an X-ray imaging system may irradiate a set of sponges. The X-ray imaging system may irradiate the sponges from the side, rather than face on, to detect the presence of the radio-opaque material (e.g., radio-opaque threads) carried by each sponge. Sponge configuration, and in particular the location of the radio-opaque material and/or transponders may substantially enhance the ability to correctly discern and count the total number of sponges in each set, packet or package. For example, various folding techniques configurations described and illustrated described herein optimally space the radio-opaque material of one sponge from the radio-opaque material of adjacent sponges. Also for example, various folding techniques and configurations described and illustrated herein optimally space the transponder with respect to the radio-opaque material.

Sets, packets or packages of sponges may be identified to represent that the count of sponges in each has been verified. For example the set of sponges may be wrapped with a band that bears an authentication symbol (e.g. trademark, logo, hologram, machine-readable symbol and/or wirelessly readable identifier).

A sponge may be summarized as including a piece of gauze folded into at least three panels which overlap with one another, including a first outer panel, a second outer panel and at least a first inner panel located interposed between the first outer panel and the second outer panel; and a first radio-opaque material carried by the first inner panel.

The piece of gauze may be folded into at least four panels which overlap with one another, including in addition to the first outer panel, the second outer panel and the first inner panel at least a second inner panel interposed between the first outer panel and the second outer panel, and may further include a second radio-opaque material carried by the second inner panel. The first radio-opaque material may be a first radio-opaque thread woven into the gauze. The first radio-opaque material may be a first radio-opaque thread attached to a face of the gauze. The first radio-opaque material may be a first radio-opaque thread attached to a face of the first inner panel that faces the first outer panel and the second radio-opaque material may be a second radio-opaque thread attached to a face of the second inner panel that faces the second outer panel. In a pre-folded configuration, the piece of gauze may have a left-most portion and a right-most portion with respect to a centerline that traverses a width of the gauze along a longitudinal length thereof, and in a folded configuration, the left-most portion of the piece of gauze may be immediately adjacent the right-most portion of the piece of gauze with respect to a thickness of the sponge.

The sponge may further include a transponder attached to the gauze.

The sponge may further include a piece of material that retains the transponder to the gauze.

The sponge may further include a closed pouch which encloses the transponder and which is attached to the gauze.

The sponge may further include a closed pouch which encloses the transponder and which is attached to the gauze via a plurality of stitches. The transponder may be an inductive-capacitive (LC) resonant circuit transponder which does not transmit any unique identifying information. The transponder may be a radio frequency identification (RFID) transponder which transmits a piece of unique identifying information in response to a radio frequency or microwave frequency interrogation signal.

A sponge may be summarized as including a piece of gauze which in a pre-folded configuration has a first major face, a second major face opposed across a thickness of the piece of gauze from the first major face, a first end, a second end, the second end opposed across a length of the piece of gauze from the first end, a first edge and a second edge, the second edge opposed across a width of the piece of gauze; a first piece of elongated radio-opaque material, extending at least partially across the width of the piece of gauze; a second piece of elongated radio-opaque material, extending at least partially across the width of the piece of gauze, the second piece of elongated radio-opaque material spaced along the length of the piece of gauze from the first piece of elongated radio-opaque material in the pre-folded configuration, the piece of gauze folded into a folded configuration with at least three fold lines to form at least four portions, the first and the second pieces of elongated radio-opaque material positioned inwardly of a pair of outermost ones of the at least four portions of the sponge with respect to a thickness of the sponge in the folded configuration; and a transponder attached to the piece of gauze. In the pre-folded configuration, the first piece of elongated radio-opaque material may be located on a first half of the piece of gauze relative to a centerline along the length of the piece of gauze and the second piece of elongated radio-opaque material may be located on the first half of the piece of gauze relative to the centerline. The first piece of elongated radio-opaque material may be a first radio-opaque thread woven into the piece of gauze and the second piece of elongated radio-opaque material may be a second radio-opaque thread woven into the piece of gauze. The first piece of elongated radio-opaque material may be a first radio-opaque thread attached to the first major face of the piece of gauze. The second piece of elongated radio-opaque material may be a second radio-opaque thread attached to the first major face of the piece of gauze. The transponder may be attached to the second major face of the piece of gauze. The first piece of elongated radio-opaque material may be a first radio-opaque thread carried by a first inner portion of the sponge in the folded configuration and the second piece of elongated radio-opaque material may be a second radio-opaque thread carried by a second inner portion of the sponge in the folded configuration, the first and the second inner portions of the sponge interposed between a first and a second outer portions of the sponge in the folded configuration. The piece of gauze may be a continuous piece of gauze, in the pre-folded configuration the piece of gauze may have a left-most portion and a right-most portion with respect to a centerline that traverses the width of the gauze along the length thereof, and in the folded configuration, the left-most portion of the piece of gauze may be immediately adjacent the right-most portion of the piece of gauze with respect to the thickness of the sponge.

The sponge may further include a piece of material that retains the transponder to the piece of gauze.

The sponge may further include a closed pouch which encloses the transponder before the transponder is attached to the piece of gauze and which is attached to the gauze.

The sponge may further include a closed pouch which encloses the transponder and which is attached to the gauze via a plurality of stitches. The transponder may be an inductive-capacitive (LC) resonant circuit transponder which does not transmit any unique identifying information. The transponder may be a radio frequency identification (RFID) transponder which may transmit a piece of unique identifying information in response to a radio frequency or microwave frequency interrogation signal.

A method of producing sponges may be summarized as including providing a piece of gauze in a pre-folded configuration, which has a first major face, a second major face opposed across a thickness of the piece of gauze from the first major face, a first end, a second end, the second end opposed across a length of the piece of gauze from the first end, a first edge and a second edge, the second edge opposed across a width of the piece of gauze, a first piece of elongated radio-opaque material, extending at least partially across the width of the piece of gauze, a second piece of elongated radio-opaque material, extending at least partially across the width of the piece of gauze, the second piece of elongated radio-opaque material spaced along the length of the piece of gauze from the first piece of elongated radio-opaque material in the pre-folded configuration, and a transponder attached to the piece of gauze; and folding the piece of gauze into a folded configuration with at least three fold lines to form at least four portions, the first and the second pieces of elongated radio-opaque material positioned inwardly of a pair of outermost ones of the at least four portions of the sponge with respect to a thickness of the sponge in the folded configuration. Folding the piece of gauze into a folded configuration may include folding the piece of gauze to have a first outer panel, a second outer panel, a first inner panel interposed between the first and the second outer panels and a second inner panel interposed between the first and the second outer panels, the first and the second pieces of elongated radio-opaque material carried by at least one of the first or the second inner panels. Folding the piece of gauze into a folded configuration may include folding the piece of gauze about a centerline of the piece of gauze with respect to the length of the piece of gauze, and then folding the piece of gauze about a centerline of the once folded piece of gauze with respect to the length of the once folded piece of gauze in a direct that locates the first and the second pieces of elongated radio-opaque material inwardly of the pair of outermost ones of the at least four portions of the sponge.

The method may further include attaching the transponder to the piece of gauze before folding the piece of gauze into the folded configuration.

The method may further include attaching the first piece of elongated radio-opaque material to the piece of gauze before folding the piece of gauze into the folded configuration.

The method may further include attaching the second piece of elongated radio-opaque material to the piece of gauze before folding the piece of gauze into the folded configuration. The first piece of elongated radio-opaque material may be a first radio-opaque thread and attaching the first piece of elongated radio-opaque material to the piece of gauze before folding the piece of gauze into the folded configuration may include attaching the first radio-opaque thread to the piece of gauze before folding the gauze into the folded configuration.

The second piece of elongated radio-opaque material may be is a second radio-opaque thread, and may further include attaching the second radio-opaque thread to the piece of gauze before folding the gauze into the folded configuration.

The method may further include providing a plurality of additional pieces of gauze in a pre-folded configuration; folding the additional pieces of gauze into respective folded configurations with at least three fold lines to form at least four portions, respective first and second pieces of elongated radio-opaque material positioned inwardly of a pair of outermost ones of the at least four portions of the respective sponges with respect to a thickness of the sponge in the folded configuration; and packaging the sponge and the additional sponges in sets of sponges.

A method of counting sponges in a set of sponges may be summarized as including presenting a set of sponges to a radiological imaging system, the set of sponges comprising a plurality of sponges, each of the sponges in the plurality of sponges comprising a respective piece of gauze folded into at least three panels which overlap with one another, including a first outer panel, a second outer panel and at least a first inner panel located interposed between the first outer panel and the second outer panel, and at least one piece of radio-opaque material carried by the first inner panel; irradiating the set of sponges with electromagnetic radiation (e.g., in the X-ray frequency range); detecting a radiological image that represents the respective at least one piece of radio-opaque material of each of the sponges in the set of sponges; and determining a total number of sponges in the set of sponges based at least in part on the detected radiological image. Irradiating the set of sponges may include irradiating the set of sponges through a respective edge of each of sponges in the set of sponges.

The method may further include providing a notification when the determined number of sponges in the set does not equal a defined number of sponges.

The method may further include applying an indication of certification to the set of sponges in response to a determination that the total number of sponges in the set is equal the defined number of sponges.

The method may further include physically coupling the set of sponges with a band in response to a determination that the total number of sponges in the set is equal the defined number of sponges, the band indicative of certification that the total number of sponges in the set is equal the defined number of sponges.

The method may further include wirelessly interrogating each the transponder of each sponge in the set of sponges; and storing a unique identifier reader from each sponge in the set of sponges in a nontransitory computer-readable memory, indicative of a determination that the total number of sponges in the set is equal the defined number of sponges.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers, and types of objects employed in medical procedures, for instance sponges, gauze or other absorbent objects, have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

For ease of understanding, a surgical environment will be used as an example environment for detecting objects but such should not be considered limiting.

FIGS. 1A-1D sequentially show a piece of gauze 100*a* being prepared to create a sponge useable in various medical procedures, according to at least one according to at least one illustrated embodiment.

Figure 1A:
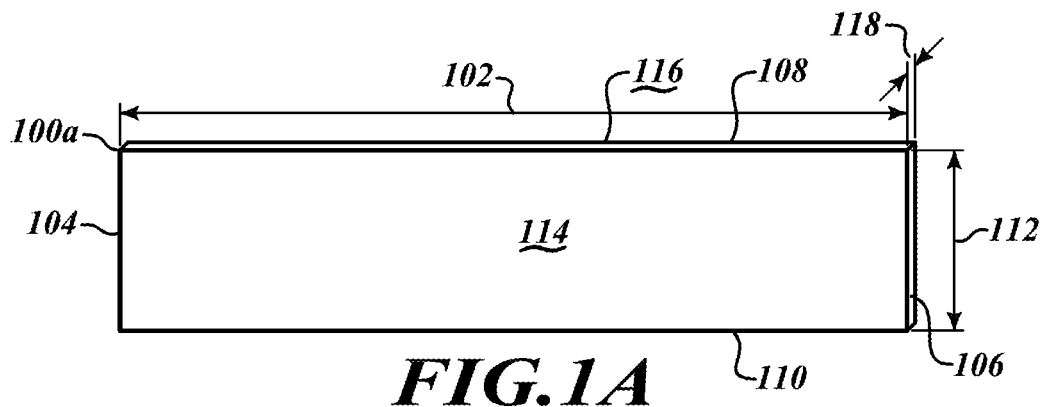
FIG. 1A is an isometric view of a piece of gauze in a pre-folded configuration, before any folding, sewing or stitching operations, according to at least one illustrated embodiment.

FIG. 1A shows the piece of gauze 100*a* in a pre-folded configuration. The piece of gauze 100*a* may comprise a loose weave of cotton preferably lint free, or may take the form of any other material suitable for use as a sponge. FIG. 1A shows the individual strands, which are omitted from the other figures to aid in clarity of illustration. The piece of gauze 100*a* may have been cut from a roll or continuous web of gauze, either manually or using automated cutting machines.

The piece of gauze 100*a* has a length 102, that extends between a first end (left-most end) 104 and a second end (right-most end) 106. The piece of gauze 100*a* has opposed edges 108, 110 across a width 112 of the piece of gauze 100*a*. The piece of gauze 100*a* has a first major face 114, and a second major face 116 opposed across a thickness 118 of the piece of gauze 100*a* from the first major face 114.

Figure 1B:
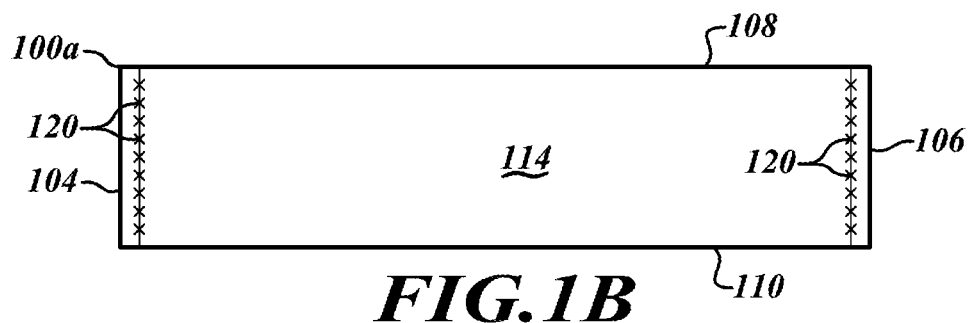
FIG. 1B is a top plan view of the piece of gauze of FIG. 1A with left-most and right-most edges optionally folded over and optionally sewn or stitched, according to at least one illustrated embodiment.

FIG. 1B shows the piece of gauze 100*a* with portions of the left-most and right-most ends 104, 106 folded over and sewn (stitches or thread indicated by the symbols X 120). Folding and swing the edges 104, 106 is optional in some embodiments, and may prevent stray threads or strands of gauze from separating from the main body.

Figure 1C:
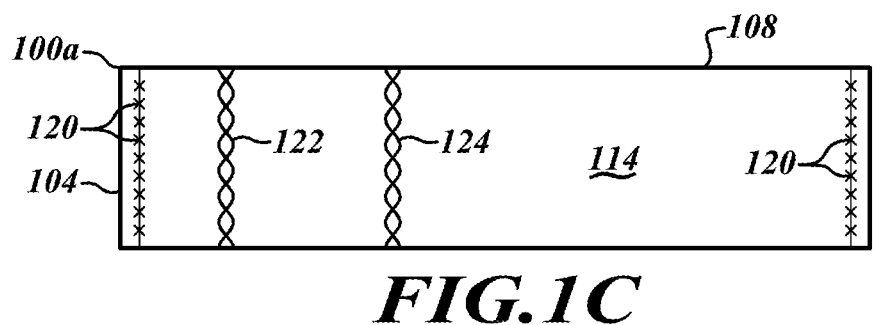
FIG. 1C is a top plan view of the piece of gauze of FIG. 1B with a first and a second radio-opaque material attached thereto according to at least one illustrated embodiment, the first second radio-opaque material extending across a width of the piece of gauze, and spaced longitudinally apart from one another.

FIG. 1C shows the piece of gauze 100*a* with a first and a second radio-opaque material 122, 124 attached thereto. The first and second radio-opaque material 122, 124 extends across at least a portion of the width 112 of the piece of gauze 100*a*, and are spaced longitudinally apart from one another along the length 102 of the piece of gauze 100*a*. The radio-opaque material 122, 124 may take a variety of forms. For example, each of the first and the second the radio-opaque material 122, 124 may take the form of one or more radio-opaque threads. The radio-opaque material 122, 124 may be attached to a major face 114, 116 of the piece of gauze 100*a*. For example, the radio-opaque material may be attached to one or both major faces 114, 116 of the piece of gauze 100*a* via a bio-compatible adhesive, heat sealing or heat welding (e.g., RF welding), via sewing or via weaving, etc. This may be particularly suitable for situations where gauze is sourced without any radio-opaque material, and is later added by a manufacturer or producer of the sponges.

Figure 1D:
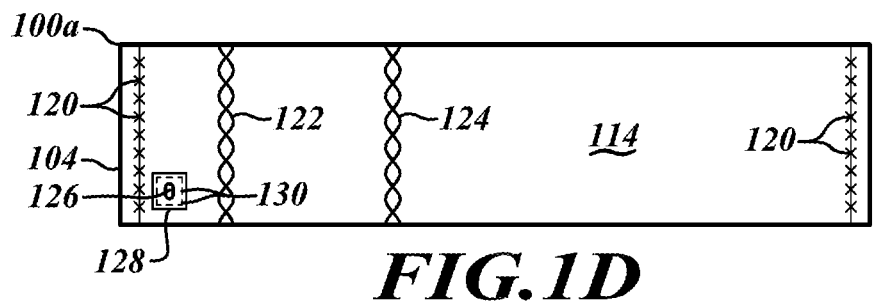
FIG. 1D is a top plan view of the piece of gauze of FIG. 1C with a first wireless transponder attached thereto, according to at least one illustrated embodiment, the first transponder positioned to overlie at least a portion of the radio-opaque material when in a folded configuration.

FIG. 1D shows the piece of gauze 100*a* with a first wireless transponder 126 attached thereto.

As described elsewhere herein, the first wireless transponder 126 may take any of a variety of forms, for example an LC resonant transponder and/or a radio frequency identification (RFID) transponder. The first transponder 126 is positioned to overlie at least a portion of the radio-opaque material 122, 124 when in a folded configuration.

The first wireless transponder 126 may be attached to the piece of gauze 100*a* via a piece of material or pouch 128, as illustrated in FIG. 1D. For example, the piece of material or pouch 128 may be attached via thread or stitches 130. Alternatively, the first wireless transponder 126 may be attached to the piece of gauze 100a via a bio-compatible adhesive, heat sealing, or heat welding (e.g., RF welding).

At this point, the piece of gauze 100a of FIG. 1D is ready for folding into a folded configuration, discussed below with reference to FIGS. 3A-3E.

Figure 2A:
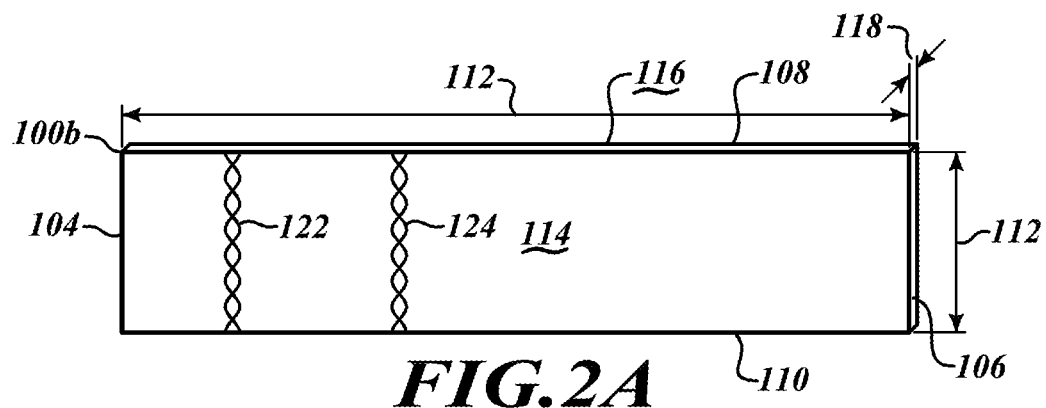
FIG. 2A is a top plan view of a piece of gauze in a pre-folded configuration, before any folding, sewing or stitching operations, according to at least one illustrated embodiment, the piece of gauze including a first and a second radio-opaque material woven therein, the first second radio-opaque material extending across a width of the piece of gauze, and spaced longitudinally apart from one another.
Figure 2B:
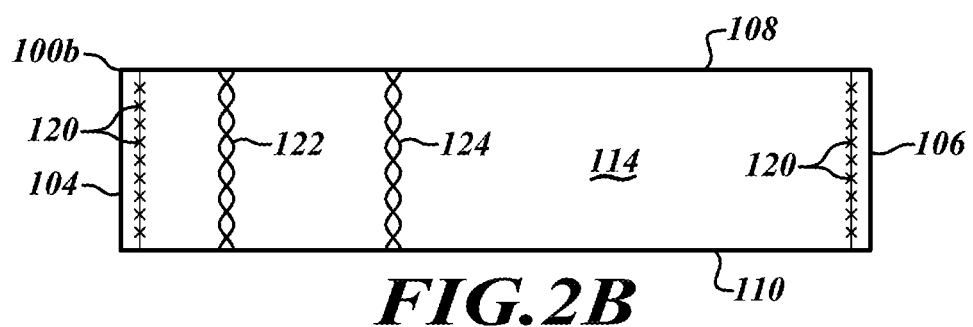
FIG. 2B is a top plan view of the piece of gauze of FIG. 2A with left-most and right-most edges optionally folded over and optionally sewn or stitched, according to at least one illustrated embodiment.
Figure 2C:
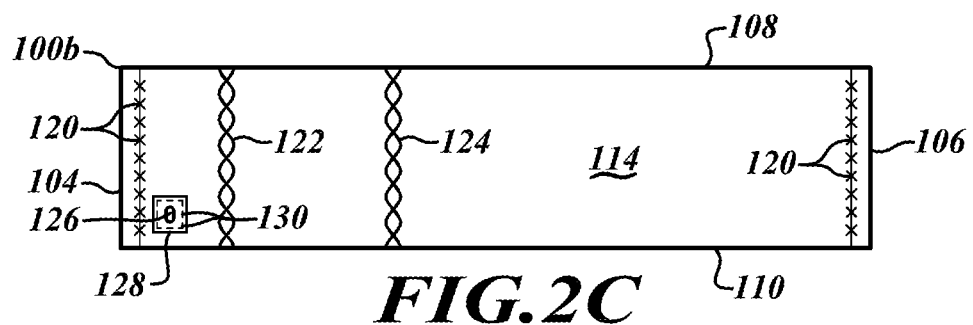
FIG. 2C is a top plan view of the piece of gauze of FIG. 2B with a first wireless transponder attached thereto, according to at least one illustrated embodiment, the first transponder positioned to overlie at least a portion of the radio-opaque material when in a folded configuration.

FIGS. 2A-2C sequentially show a piece of gauze 100b being prepared to create a sponge useable in various medical procedures, according to at least one according to at least one illustrated embodiment.

FIG. 2A shows the piece of gauze 100b in a pre-folded configuration, before any folding, sewing or stitching operations. The piece of gauze 100b may be similar or even identical in many or most respects to the piece of gauze (FIG. 1A). Such similar or even identical structures are referenced using the same reference numbers as employed in FIGS. 1A-1D. Most notably, the piece of gauze 100b includes a first and a second radio-opaque material 122, 124 woven therein.

The first second radio-opaque material 122, 124 extend across the width 112 of the piece of gauze 100b, and are spaced longitudinally apart from one another along the length 102 of the piece of gauze 100b. In some instances, gauze may be sourced with radio-opaque material woven therein, which typically occurs during creation of the gauze. Alternatively, the manufacture of the sponge may weave the radio-opaque material therein after the gauze has been woven.

FIG. 2B is a top plan view of the piece of gauze 100b of FIG. 2A with portions of the left-most and right-most ends 104, 106 optionally folded over and optionally sewn or stitched 120, according to at least one illustrated embodiment.

FIG. 2C is a top plan view of the piece of gauze 100b of FIG. 2B with a first wireless transponder 126 attached thereto, according to at least one illustrated embodiment, the first wireless transponder 126 positioned to overlie at least a portion of the radio-opaque material 122, 124 when in a folded configuration.

FIGS. 3A-3D sequentially show a piece of gauze 100a, 100b being folded from a pre-folded configuration into a folded configuration as a sponge 300, according to at least one illustrated embodiment. In the particular folded configuration illustrated, the sponge 300 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

Figure 3A:
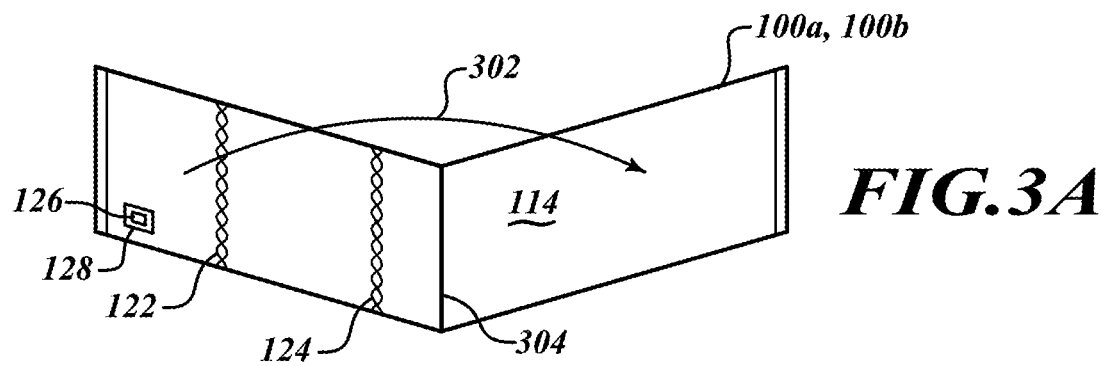
FIG. 3A shows a piece of gauze similar or even identical to those of FIGS. 1D and 2C with first and second radio-opaque material and a wireless transponder, being folded across a first fold-line, according to at least one illustrated embodiment.

FIG. 3A shows a piece of gauze 100a, 100b similar or even identical to those of FIGS. 1D and 2C, with first and second radio-opaque material 122, 124 and a wireless transponder 126. Similar or even identical structures to previous illustrated embodiments are referenced using the same reference numbers as previously employed. Notably, the first and second radio-opaque material 122, 124 are positioned on a same half of the piece of gauze 100a, 100b with respect to a longitudinal middle or center of the piece of gauze 100a, 100b (i.e., middle along the longitudinal axis as the piece of gauze lies flat). As illustrated by arrow 302 in FIG. 3A, a first portion or panel of the piece of gauze 100a, 100b is folded across a first fold-line 304 such that two resulting portions of the first major face 114 are brought together, facing one another.

Figure 3B:
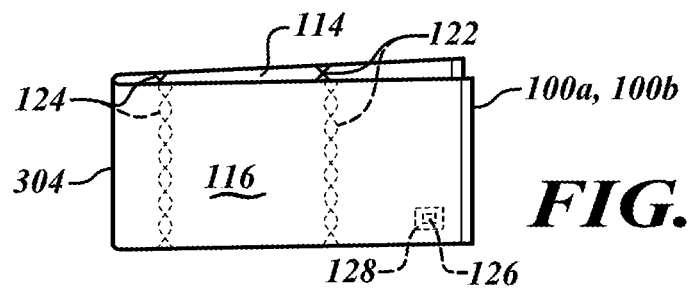
FIG. 3B shows the piece of gauze of FIG. 3A folded across the first fold-line, one half of the piece of gauze overlying the other half of the piece of gauze, according to at least one illustrated embodiment.

FIG. 3B shows the piece of gauze 100a, 100b of FIG. 3A folded across the first fold-line 304, one half of the piece of gauze 100a, 100b overlying the other half of the piece of gauze 100a, 100b. As illustrated in FIG. 3B, the second major face 116 is on an exterior the partially folded piece of gauze 100a, 100b, while the first major face 114 is now on an interior of the partially folded piece of gauze 100a, 100b. Notably, the first and second radio-opaque material 122, 124 are positioned on respective halves of the partially folded piece of gauze 100a, 100b with respect to a longitudinal middle or center of the partially folded piece of gauze 100a, 100b.

Figure 3C:
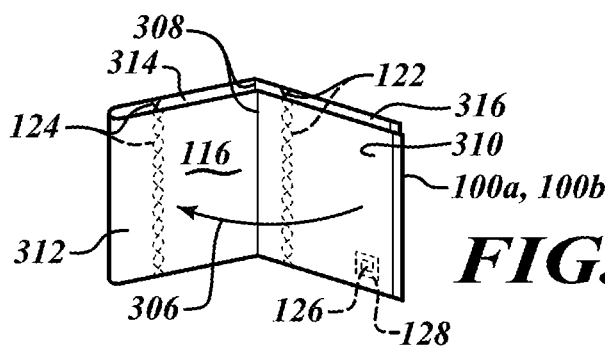
FIG. 3C shows the piece of gauze of FIG. 3B being folded across a second fold-line, according to at least one illustrated embodiment.

As illustrated by arrow 306 in FIG. 3C, the piece of gauze 100a, 100b is folded across a second fold-line 308 such that the two halves of the first major face 114 of the partially folded piece of gauze 100a, 100b are brought together, facing one another.

Figure 3D:
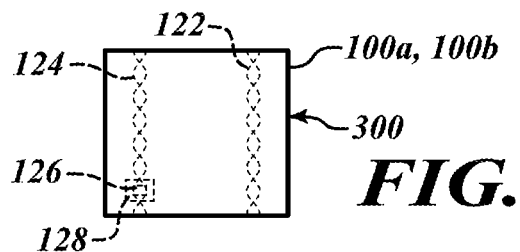
FIG. 3D shows the piece of gauze of FIG. 3C folded across the second fold-line in a folded configuration, four portions of the piece of gauze overlying one another with the radio-opaque material on respective inner pieces or panels of the piece of gauze with respect to a pair of outer pieces or panels of the piece of gauze, according to at least one illustrated embodiment.
Figure 3E:
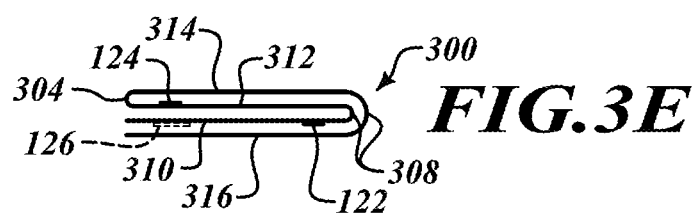
FIG. 3E is top elevational view of the piece of gauze of FIG. 3D in the folded configuration, better illustrating the four portions of the piece of gauze overlying one another with the radio-opaque material on respective inner pieces or panels of the piece of gauze with respect to a pair of outer pieces or panels of the piece of gauze.

FIGS. 3D and 3E show the piece of gauze 100a, 100b of FIG. 3C folded across the second fold-line 304 in a folded configuration, four portions of the piece of gauze 100a, 100b overlying one another. Notably, the radio-opaque material is carried by respective inner pieces or panels 310, 312 of the piece of gauze 100a, 100b or sponge 300, with respect to a pair of outer pieces or panels 314, 316 of the piece of gauze 100a, 100b or sponge 300. As best seen in FIG. 3E, the sponge 300 includes two folds and results in four pieces or panels overlying one another, in a nested configuration, with the radio-opaque material 122, 124 spaced relatively inward of the outer most panels or pieces 314, 316 and on distinctly panels or pieces 310, 312 from one another, advantageously enhancing detectability using imaging techniques. Further, the transponder 126 may overlie one of the radio-opaque material 122, 124 when viewed from a resulting major face of the sponge 300, again advantageously enhancing detectability.

Figure 4:
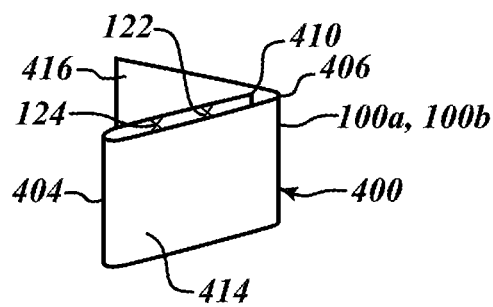
FIG. 4 is an isometric view showing a piece of gauze similar or identical to those of FIG. 1D or 2C folded across two fold-lines in a folded configuration, three portions of the piece of gauze overlying one another with the radio-opaque material on an inner piece or panel of the piece of gauze with respect to a pair of outer pieces or panels of the piece of gauze, according to at least one illustrated embodiment.

FIG. 4 shows piece of gauze 100a, 100b being folded from a pre-folded configuration into a folded configuration as a sponge 400, according to at least one illustrated embodiment. In the particular folded configuration illustrated, the sponge 400 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

The piece of gauze 100a, 100b is similar or identical to those of FIG. 1D or 2C. Similar or even identical structures to previous illustrated embodiments are referenced using the same reference numbers as previously employed.

The piece of gauze 100a, 100b is folded across two fold-lines 404, 406 in a folded configuration. This results in three portions or panels 410, 412, 414 of the piece of gauze overlying one another. Notably, the radio-opaque material 122, 124 is carried on a resulting inner piece or panel 410 of the piece of gauze 100a, 100b with respect to a pair of outer pieces or panels 414, 416 of the piece of gauze 100a, 100b. This again advantageously positions the radio-opaque material 122, 124 and/or transponder 126 (not visible in FIG. 4) to enhance detectability.

Figure 5:
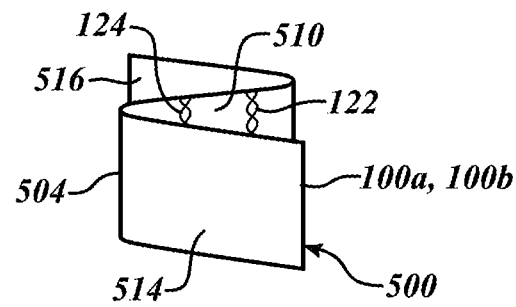
FIG. 5 is an isometric view showing a piece of gauze similar or identical to those of FIG. 1D or 2C folded across two fold-lines in a folded configuration, three portions of the piece of gauze overlying one another with the radio-opaque material on an inner piece or panel of the piece of gauze with respect to a pair of outer pieces or panels of the piece of gauze, according to at least one illustrated embodiment.

FIG. 5 shows piece of gauze 100a, 100b being folded from a pre-folded configuration into a folded configuration as a sponge 500, according to at least one illustrated embodiment. In the particular folded configuration illustrated, the sponge 500 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

The piece of gauze 100a, 100b is similar or identical to those of FIG. 1D or 2C. Similar or even identical structures to previous illustrated embodiments are referenced using the same reference numbers as previously employed.

The piece of gauze 100a, 100b is folded across two fold-lines 504, 506 in a folded configuration. This results in three portions or panels 510, 512, 514 of the piece of gauze 100a, 100b overlying one another. Notably, the radio-opaque material 122, 124 is carried on a resulting inner piece or panel 510 of the piece of gauze 100a, 100b with respect to a pair of outer pieces or panels 514, 516 of the piece of gauze 100a, 100b. This again advantageously positions the radio-opaque material 122, 124 and/or transponder 126 (not visible in FIG. 5) to enhance detectability.

Figure 6:
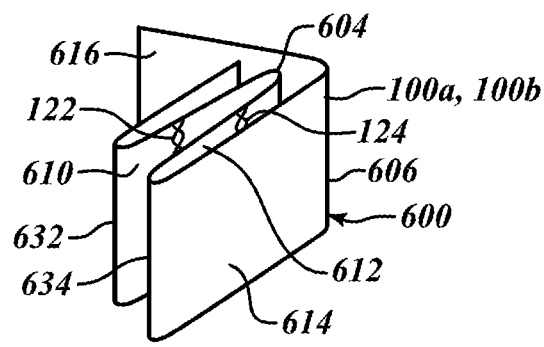
FIG. 6 is an isometric view showing a piece of gauze similar or identical to those of FIG. 1D or 2C folded across four fold-lines in a folded configuration, five portions of the piece of gauze overlying one another with the radio-opaque material on respective inner pieces or panels of the piece of gauze with respect to a pair of outer pieces or panels of the piece of gauze, according to at least one illustrated embodiment.

FIG. 6 shows piece of gauze 100a, 100b being folded from a pre-folded configuration into a folded configuration as a sponge 600, according to at least one illustrated embodiment. In the particular folded configuration illustrated, the sponge 600 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

The piece of gauze 100a, 100b is similar or identical to those of FIG. 1D or 2C. Similar or even identical structures to previous illustrated embodiments are referenced using the same reference numbers as previously employed.

The piece of gauze is folded across four fold-lines 604, 606, 632, 634 in a folded configuration. This results in five portions or panels 610, 612, 614, 616 (only four called out in FIG. 6) of the piece of gauze 100a, 100b overlying one another. Notably, the radio-opaque material 122, 124 is carried on respective resulting inner pieces or panels 610, 612 of the piece of gauze 100a, 100b with respect to a pair of outer pieces or panels 614, 616 of the piece of gauze 100a, 100b. This again advantageously positions the radio-opaque material 122, 124 and/or transponder 126 (not visible in FIG. 6) to enhance detectability.

Figure 7:
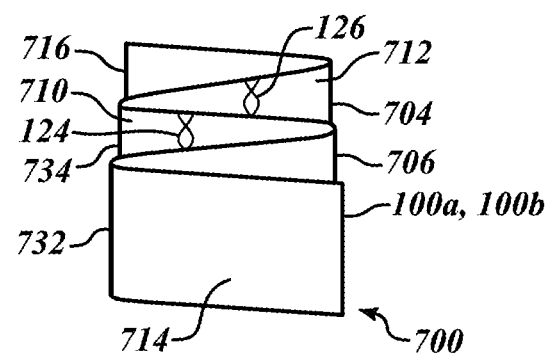
FIG. 7 is an isometric view showing a piece of gauze similar or identical to those of FIG. 1D or 2C folded across four fold-lines in a folded configuration, five portions of the piece of gauze overlying one another with the radio-opaque material on respective inner pieces or panels of the piece of gauze with respect to a pair of outer pieces or panels of the piece of gauze, according to at least one illustrated embodiment.

FIG. 7 shows piece of gauze 100a, 100b being folded from a pre-folded configuration into a folded configuration as a sponge 700, according to at least one illustrated embodiment. In the particular folded configuration illustrated, the sponge 700 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

The piece of gauze 100a, 100b is similar or identical to those of FIG. 1D or 2C. Similar or even identical structures to previous illustrated embodiments are referenced using the same reference numbers as previously employed.

The piece of gauze 100a, 100b is folded across four fold-lines 704, 706, 732, 734 in a folded configuration. This results in five portions or panels 710, 712, 714, 716 (only four called out in FIG. 7) of the piece of gauze 100a, 100b overlying one another. Notably, the radio-opaque material 122, 124 is carried on respective resulting inner pieces or panels 710, 712 of the piece of gauze 100a, 100b with respect to a pair of outer pieces or panels 714, 716 of the piece of gauze 100a, 100b. This again advantageously positions the radio-opaque material 122, 124 and/or transponder 126 (not visible in FIG. 7) to enhance detectability.

Figure 8:
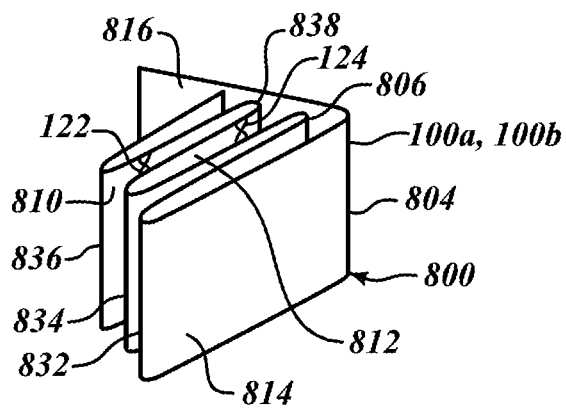
FIG. 8 is an isometric view showing a piece of gauze similar or identical to those of FIG. 1D or 2C folded across six fold-lines in a folded configuration, seven portions of the piece of gauze overlying one another with the radio-opaque material on respective inner pieces or panels of the piece of gauze with respect to a pair of outer pieces or panels of the piece of gauze, according to at least one illustrated embodiment.

FIG. 8 shows piece of gauze 100a, 100b being folded from a pre-folded configuration into a folded configuration as a sponge 800, according to at least one illustrated embodiment. In the particular folded configuration illustrated, the sponge 800 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

The piece of gauze 100a, 100b is similar or identical to those of FIG. 1D or 2C. Similar or even identical structures to previous illustrated embodiments are referenced using the same reference numbers as previously employed.

The piece of gauze 100a, 100b is folded across six fold-lines 804, 806, 832, 834, 836, 838 in a folded configuration. This results in seven portions or panels 810, 812, 814, 816 (only four called out in FIG. 8) of the piece of gauze 100a, 100b overlying one another. Notably, the radio-opaque material 122, 124 is carried on respective resulting inner pieces or panels 810, 812 of the piece of gauze 100a, 100b with respect to a pair of outer pieces or panels 814, 816 of the piece of gauze 100a, 100b. This again advantageously positions the radio-opaque material 122, 124 and/or transponder 126 (not visible in FIG. 8) to enhance detectability.

Figure 9:
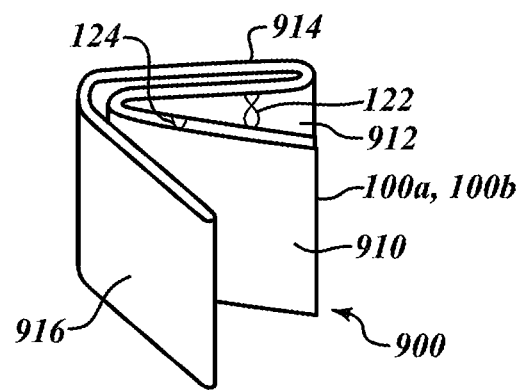
FIG. 9 is an isometric view showing a piece of gauze similar or identical to those of FIG. 1D or 2C folded three times into a folded configuration, eight portions of the piece of gauze overlying one another with the radio-opaque material on respective inner pieces or panels of the piece of gauze with respect to a pair of outer pieces or panels of the piece of gauze, according to at least one illustrated embodiment.

FIG. 9 shows piece of gauze 100a, 100b being folded from a pre-folded configuration into a folded configuration as a sponge 900, according to at least one illustrated embodiment. In the particular folded configuration illustrated, the sponge 900 may advantageously be easier to detect and/or distinguish from neighboring sponges in a set, packet or package of sponges, using imaging techniques, described herein, due to the resulting orientation and/or spacing of radio-opaque material 122, 124 and/or wireless transponder 126.

The piece of gauze 100a, 100b is similar or identical to those of FIG. 1D or 2C. Similar or even identical structures to previous illustrated embodiments are referenced using the same reference numbers as previously employed.

The piece of gauze 100a, 100b is folded in half, the resulting partially folded piece of gauze 100a, 100b is folded in half again, and then the partially folded piece of gauze 100a, 100b is folded in half a further time. This results in eight portions or panels 910, 912, 914, 916 (only four called out in FIG. 9) of the piece of gauze 100a, 100b overlying one another. Notably, the radio-opaque material 122, 124 is carried on respective resulting inner pieces or panels 910, 912 of the piece of gauze 100a, 100b with respect to a pair of outer pieces or panels 914, 916 of the piece of gauze 100a, 100b. This again advantageously positions the radio-opaque material 122, 124 and/or transponder 126 (not visible in FIG. 9) to enhance detectability.

Figure 10:
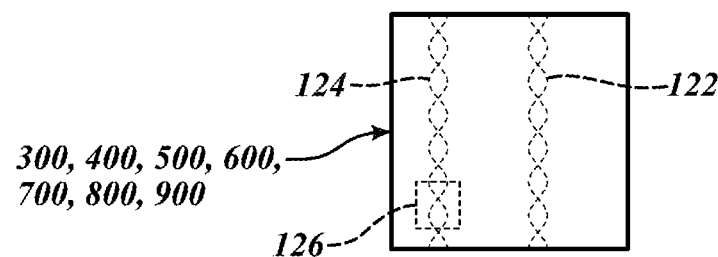
FIG. 10 is a front plan view showing a piece of gauze similar or identical to those of any of FIGS. 4-9, illustrating the relative positioning of the radio-opaque material with respect to the wireless transponder, according to at least one illustrated embodiment.

FIG. 10 shows a sponge 300, 400, 500, 600, 700, 800, 900 in a folded configuration. Such illustrates the relative positioning of the radio-opaque material 122, 124 on inner portions of the sponge relative to outer portions thereof. Such also illustrate the relative positioning of a wireless transponder 126 relative to at least one of the radiopaque material 122, 124.

Figure 11:
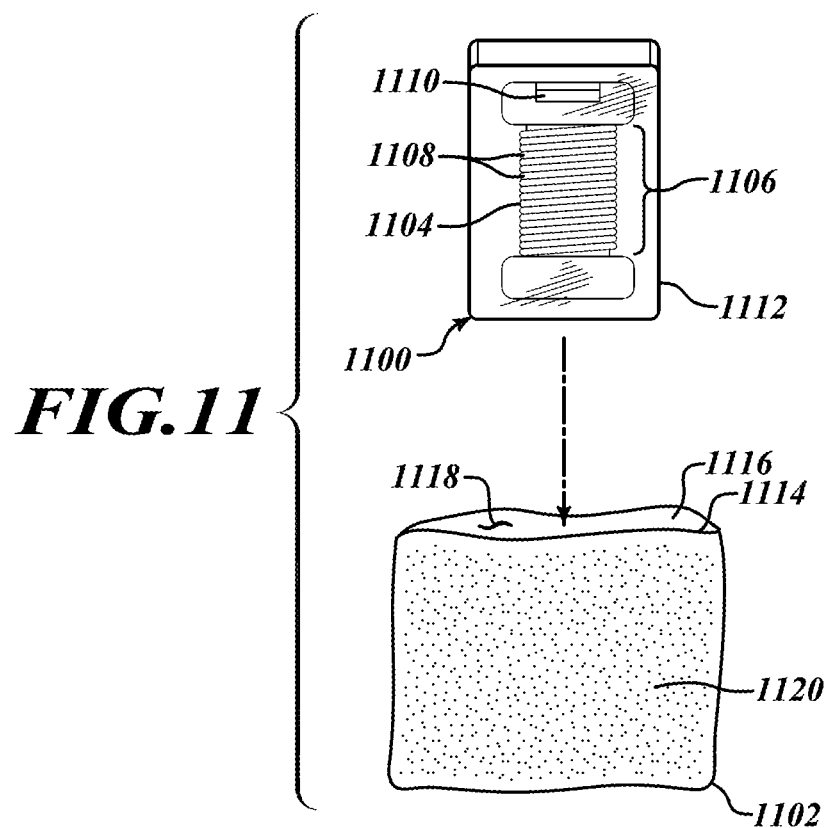
FIG. 11 is a schematic view showing an LC resonant transponder and pouch in which the LC resonant transponder may be sealed, either before or following attachment to a piece of gauze.

FIG. 11 shows an LC resonant transponder 1100 and pouch 1102 in which the LC resonant transponder 1100 may be sealed, either before or following attachment to a piece of gauze 100a, 100b (FIGS. 1A-1D, 2A-2D).

The LC resonant transponder 1100 may comprise a core 1104, for example a ferrite core. The core 1104 may, for example take the form of a dumbbell-shaped ferrite rod having broad end portions and a narrow intermediate portion. The broad end portions may provide capacitive functionality. In other implementations, the core 1104 may be shaped as a fusiform-shaped object, with truncated ends.

The LC resonant transponder 1100 may comprise an inductor 1106 formed by a winding which includes a plurality of coils 1108 of an electrically conductive material wrapped around the core 1104. The electrically conductive material may, for example, take the form of electrically conductive wire, for instance copper wire.

The LC resonant transponder 1100 may comprise a capacitor or inherent capacitance 1110, electrically coupled to the inductor 1106. The inductance of the inductor 1106 and the capacitance of the capacitor 1110 are selected to achieved a desired resonant frequency for the LC resonant transponder 1100 (e.g., 145 kHz). For example, the inductive coil and capacitor may together form an inductive/capacitance (L/C) tank circuit. Additional details about types of transponders may be found in U.S. Provisional Patent Application Ser. No. 60/811,376 filed Jun. 6, 2006 and U.S. Provisional Patent Application Ser. No. 60/892,208, filed Feb. 28, 2007, both of which are incorporated herein by reference.

The LC resonant transponder 1100 may be enclosed in an encapsulant or housing 1112 to provide environmental protection to the circuit, and/or to isolate the circuit from bodily tissue. The encapsulant or housing 1112 may advantageously protect the transponder from the ambient environment, for instance from forces, pressure and/or fluids, such as bodily fluids. The encapsulant or housing 1112 preferably comprises a bio-compatible material. The LC resonant transponder 1100 may be relatively small, for example approximately 5-12 millimeters long with a diameter of about 1-4 millimeters.

As previously mentioned, the LC resonant transponder 1100 does not store, encode or otherwise transmit any unique identifying information. As such, the presence transponder 122 may be denominated as a "dumb" transponder. The LC resonant transponder 1100 acts as a simple presence/absence transponder, radiating a return signal in an approximate frequency range when excited by an interrogation signal in or proximate a defined frequency range. The frequency ranges of the interrogation and return signals may be the same or approximately the same (e.g., overlapping). Alternatively, the frequency ranges of the interrogation and return signals may be different from one another (e.g., not overlapping). Lower frequencies may enable superior transmission of signals through bodily tissues or other obstacles including membranes, skin, flesh, etc. Thus, in vivo LC resonant transponder 1100 may be more readily detectable as compared to an in vivo RFID transponder, which typically operate at higher frequencies (e.g., UHF) as compared to an LC resonant transponder 1100.

The pouch 1102 is typically made of material, and forms an interior cavity or interior 1118, into which the LC resonant transponder 1100 and/or an RFID transponder 1200 (FIG. 12) may be received and retained.

The pouch 1102 is physically coupleable to a piece of gauze 100*a*, 100*b* (FIGS. 1A-1D, 2A-2D), to attach the LC resonant transponder 1100 and/or an RFID transponder 1200 (FIG. 12) to the retain the piece of gauze 100*a*, 100*b*. As previously noted, the LC resonant transponder 1100 and/or an RFID transponder 1200 (FIG. 12) may be closed or sealed in the interior 1118 of the pouch 1102 before the pouch 1102 is attached or secured to the piece of gauze 100*a*, 100*b* (FIGS. 1A-1D, 2A-2D). This may facilitate the economic production of large numbers of sponges. Alternatively, one or both the LC resonant transponder 1100 and/or an RFID transponder 1200 (FIG. 12) may be closed or sealed in the interior 1118 of the pouch 1102 after the pouch 1102 is attached or secured to the piece of gauze 100*a*, 100*b* (FIGS. 1A-1D, 2A-2D).

In some implementations, the LC resonant transponder 1100 is freely movable within the interior of the pouch 1102. Such may advantageously allow folding, stretching, compression, twisting, or other physical manipulation of the piece of gauze 100*a*, 100*b* or sponge without causing damage to the LC resonant transponder 1100. For example, the LC resonant transponder 1100 freely moves within the pouch 1102 to an advantageous position experiencing reduced forces. Likewise, the free-floating LC resonant transponder 1100 does not inhibit folding, stretching, compression, twisting, or other physical manipulation of the piece of gauze 100*a*, 100*b* or sponge 300, 400, 500, 600, 700, 800, 900 which may be necessary for the medical procedure.

The RFID transponder 1200 (FIG. 12) may freely movable within the interior of the pouch 1102. Alternatively, the RFID transponder 1200 (FIG. 12) may be fixed in the interior 1118 of the pouch 1102. Alternatively, the RFID transponder 1200 (FIG. 12) may form a portion of the pouch 1102. For example, a substrate of an RFID transponder 1200 (FIG. 12) may form one of the layers 1114, 1116 of the pouch 1102 or may be incorporated or laminated into one of the layers 1114, 1116 of the pouch 1102. One or more portions of the pouch 1102 may form one or more directional antenna elements to cooperate with an antenna of the RFID transponder 1200. Details of such is described in U.S. provisional patent application Ser. No. 62/106,052 filed Jan. 21, 2015; and in U.S. provisional patent application Ser. No. 62/138,248 filed Mar. 25, 2015.

The pouch 1102 may be made of any of variety of materials, including textiles, for instance woven or knitted textiles, or membranes, for instance unreinforced or reinforced polymer membranes, or a combination of such. For example, the pouch 1102 may include a first layer 1114 and second layer 1116 that forms the interior 1118 therebetween. The first layer 1114 can be physically coupled to a surface of the piece of gauze 100*a*, 100*b*.

The pouch 1102 may be attached to the piece of gauze 100*a*, 100*b* via thread for example sewn to the piece of gauze 100*a*, 100*b* using one or more stitches 130 (FIGS. 1D, 2C).

Additionally or alternatively, the pouch 1102 may optionally include, or may interact with, an adhesive layer 1120 to physically adhere or otherwise attach the pouch 1102 to a piece of gauze 100*a*, 100*b*. The adhesive layer 1120 may retain structural and adhesive integrity at least at temperatures equal to 121, 130, 132, 136, and/or 150 degrees Centigrade or higher. For example, the adhesive layer 1120 may not melt or otherwise liquefy and may retain adhesion to the first layer 1114, second layer 1116 and/or the piece of gauze 100*a*, 100*b* at temperatures less than or equal to 121, 130, 132, 136, and/or 150 degrees Centigrade or higher. This may permit the pouch 1102 and/or sponge to be sterilized.

Additionally or alternatively, the pouch 1102 may optionally be attached to the piece of gauze 100*a*, 100*b* via heat welding, e.g., via a radio frequency (RF) weld.

Additionally or alternatively, the pouch 1102 may optionally be attached to the piece of gauze 100*a*, 100*b* via an epoxy, preferably a biocompatible epoxy.

The interior 1118 of the pouch 1102 may be closed or sealed via thread, for example sewn shut using one or more stitches (not shown). Additionally or alternatively, the interior 1118 of the pouch 1102 may be closed or sealed via an adhesive, for instance an adhesive that retains structural integrity at least at temperatures equal to 121, 130, 132, 136, and/or 150 degrees Centigrade or higher. Additionally or alternatively, the interior 1118 of the pouch 1102 may be closed or sealed via may optionally be attached to the piece of gauze 100a, 100b via heat welding, e.g., via a radio frequency (RF) weld.

The first and/or second layers 1114 and 1118 may be fabric laminates or other materials. For example, the first and/or second layers 1114 and 1118 may be one or more of thermoplastic polyurethane (TPU) and nylon fabric; polyvinyl chloride (PVC) impregnated fabric; layer(s) of PVC, TPU, PET, PETG, LDPE, EVA, open celled polyurethanes, or nylon; other fabrics (e.g., cotton, polyester, leather, vinyl, polyethylene, and blended fabrics); other plastics; or combinations thereof. The first and/or second layers 1114 and 1118 are typically relatively thin and may be absorbent or non-absorbent. In some implementations, the first and/or second layers 1114 and 1118 are a material suitable to prevent entry of fluids into the interior cavity of the pouch 1102 (e.g., due to a water-proof or water-resistant coating). Thus, the first and/or second layers 1114 and 1118 may be soft, pliable, and resistant to ripping or tearing.

In one particular example, the first layer 1114 includes a first layer of TPU and a first layer of nylon fabric. The second layer 1116 includes a second layer of TPU and a second layer of nylon fabric. For example, the first and second layers of TPU may respectively be located interior relative to the first and second layers of nylon fabric. In other words, the first and second layers of TPU may contact each other and may form an interior surface of the interior cavity 1118 of the pouch 1102 while the first and second layers of nylon fabric are respectively carried by respective exterior surfaces of the first and second layers of TPU that are opposite to the interior cavity 1118. Such may advantageously allow the first and second layers of TPU to more completely melt together or otherwise physically couple to each other when an RF weld is generated. However, in other implementations, the first and second layers of nylon fabric may be located interior relative to the first and second layers of TPU or may be embedded within the first and second layers of TPU.

Suitable adhesive for the adhesive layer 1120 or to join the first and second layers 1114, 1116 together may include is a hot melt adhesive. For example, the pouch 1102 may be constructed at least in part by causing the temperature of at least a portion the hot melt adhesive to exceed a melting point temperature associated with the hot melt adhesive, thereby causing such portion to at least in part melt. For example, such may be performed using an RF welding machine, planar heat pressing machine, hot-air welding machine, or laminator. Alternatively, the pouch 1102 may be baked (e.g., in a chamber) or exposed to various other techniques for applying heat and/or pressure at desired locations. Generally, the melting point temperature will be at least greater than 130 degrees Centigrade.

The hot melt adhesive is preferably a high temperature hot melt adhesive (i.e., a hot melt adhesive that has a relatively high melting point temperature). For example, the hot melt adhesive may have a melting point temperature of greater than 121, 130, 132, or 136 degrees Centigrade. As another example, the hot melt adhesive layer may have a melting point temperature of about 150 degrees Centigrade or higher. Such may advantageously enhance the ability to sterilize the pouch 1102 or sponge. More particularly, the hot melt adhesive may have a melting point temperature greater than a sterilization temperature associated with one or more sterilization procedures. For example, the hot melt adhesive may have a melting point temperature greater than a steam temperature at which a volume of steam is maintained during one or more steam-based sterilization procedures at some defined pressure. For example, two common steam-based sterilization techniques use a volume of steam respectively maintained at 121 degrees Centigrade (250 degrees Fahrenheit) and 132 degrees Centigrade (270 degrees Fahrenheit). The hot melt adhesive may have a melting point temperature greater than one or both of such temperatures. Further, certain sterilization procedures may be performed with pressure conditions greater than 1 atmosphere. The hot melt adhesive may any of the melting point temperature characteristics described herein at such pressure conditions.

The adhesive is preferably biocompatible, permitting use in vivo.

The adhesive may, for example, take the form of an adhesive web film. The adhesive may, for example, take the form of a thermal lamination film. The adhesive may, for example, take the form of a meltable plastic layer, such as, for example, a thermoplastic layer. The adhesive may be a thermosetting plastic, that has an initial cure temperature at which the thermosetting plastic layer cures. For example, the initial cure temperature may be less than 130 degrees Centigrade. Subsequent to curing, the thermosetting plastic layer may retain structural and adhesive integrity at least at temperatures less than or equal to 121, 130, 132, 136, and/or 150 degrees Centigrade or higher. The adhesive may be a heat-activated adhesive layer. Alternatively or additionally, the adhesive pressure-activated adhesive layer or a pressure-sensitive adhesive layer. Alternatively or additionally, the adhesive may be a water-activated adhesive. The adhesive may, for example, include one or more of a thermoplastic polyurethane, silicone, polyamide, polyethersulfone, polyethylene, polypropylene, and ethylene vinyl acetate.

Figure 12:
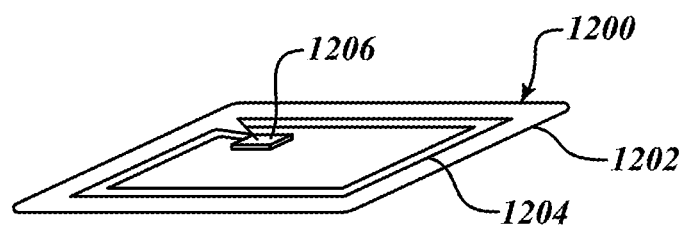
FIG. 12 is an isometric view of a radio frequency identification (RFID) transponder, which may be received in or form a portion of the pouch of FIG. 11, or otherwise attached to a piece of gauze.

FIG. 12 shows a radio frequency identification (RFID) transponder 1200, according to one illustrated embodiment.

The RFID transponder 1200 may be received in or form a portion of the pouch 1102 of FIG. 11, or otherwise attached to a piece of gauze.

The RFID transponder 1200 may include a substrate 1202. For example, the RFID transponder 1200 may include an electrically insulative substrate (e.g., polyester) with one or more electrically conductive traces and/or vias. The substrate 1202 may, for example, take the form of or otherwise comprise a flexible printed circuit board.

The RFID transponder 1200 may include one or more antennas 1204. For example, the RFID transponder 1200 may include a printed or otherwise deposited or etched electrically conductive trace as an antenna 1204 or antenna element. Any of a variety of types of antennas may be employed, for instance a spiral or coil antenna or a T-shaped dipole antenna.

The RFID transponder 1200 may include one or more circuits 1206, carried by the substrate and communicatively coupled to the one or more antennas. Circuits 1206 may take the form of integrated circuits and/or analog or digital circuit elements. Where the RFID transponder 1200 is a passive RFID transponder 1200, the circuit 1206 may include a front end power converter that converts energy from an interrogation signal (e.g., radio frequency, microwave frequency), into DC power to charge a capacitor and power the operation of the RFID transponder 1200. The circuit 1206 may include memory or storage that encodes a unique identifier (i.e., unique over a set of all otherwise identical RFID transponders 1200), which is returned from the RFID transponder 1200 in response to receipt of an interrogation signal, for instance via backscattering.

Even where the identifier is unique, some portion of the identification information or some other identification information may not be unique, for example, a portion representing a manufacturer, a lot, or a type, may be shared between transponders 1200 from the same manufacturer, lot or of the same type. In some implementations, the identification information can be associated with a type of the sponge (e.g., "lap sponge") or an attribute thereof. For example, the identification information can be linked to the type or attribute using a database, lookup table, or other data structure that cross-references unique identifiers with the type or attribute.

Alternatively, in implementations where the integrated circuit of the RFID transponder 1200 has read and write capability, the identification information can include the desired attribute, pre-stored or written onto the integrated circuit, and directly convey the pre-stored attribute via the first response signal.

Furthermore, in some implementations, the RFID transponder 1200 is a printable and/or ultra-low-cost RFID transponder 1200 that is not necessarily intended to maintain functionality when the sponge used within the surgical environment. In such implementations, the RFID transponder 1200 is interrogated at a conclusion of or during a manufacturing process, for example, to ensure that an appropriate number of sponges are included in a set, packet or package. After such use, the RFID transponder 1200 may not be expected to provide further use and may allowably degrade or otherwise experience damage if the sponge is used within the surgical environment (e.g., in vivo). Such may permit inclusion of low-cost RFID transponders 1200 for use in manufacturing without requiring a hardened or rugged encapsulant or transponder body to protect the transponders 1200 during surgical procedures. Further, the RFID transponder 1200 may be intentionally exposed to Gamma radiation to render the RFID transponder 1200 inoperative prior to delivery or use in a clinical setting.

Figure 13:
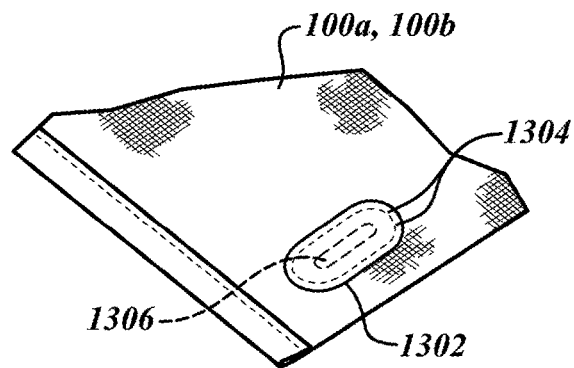
FIG. 13 is an isometric view of a portion of a piece of gauze with a pouch similar or even identical to the pouch of FIG. 11 sewn or stitched to the piece of gauze and enclosing a wireless transponder, according to at least one illustrated embodiment.

FIG. 13 shows a portion of a piece of gauze 100*a*, 100*b* with a pouch 1302 similar or even identical to the pouch 1102 of FIG. 11 sewn or stitched 1304 to the piece of gauze 100*a*, 100*b* and enclosing one or more wireless transponders 1306, according to at least one illustrated embodiment. The wireless transponders 1306 may, for example include one or more LC resonant transponders and/or one or more RFID transponders.

Figure 14:
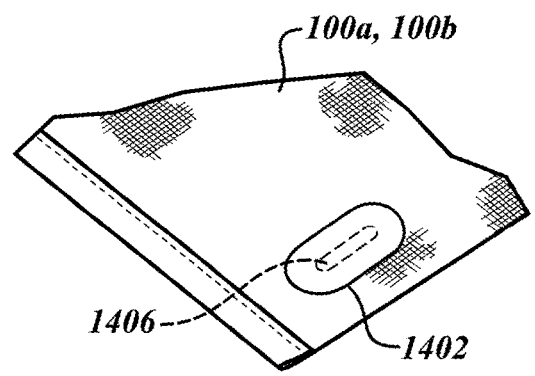
FIG. 14 is an isometric view of a portion of a piece of gauze with a pouch similar or even identical to the pouch of FIG. 10 adhered or heat sealed to the piece of gauze and enclosing a wireless transponder, according to at least one illustrated embodiment.

FIG. 14 shows a portion of a piece of gauze 100*a*, 100*b* with a pouch 1402 similar or even identical to the pouch 1102 of FIG. 11 adhered or heat sealed to the piece of gauze and enclosing a wireless transponder 1406, according to at least one illustrated embodiment. The wireless transponders 1406 may, for example include one or more LC resonant transponders and/or one or more RFID transponders.

Figure 15:
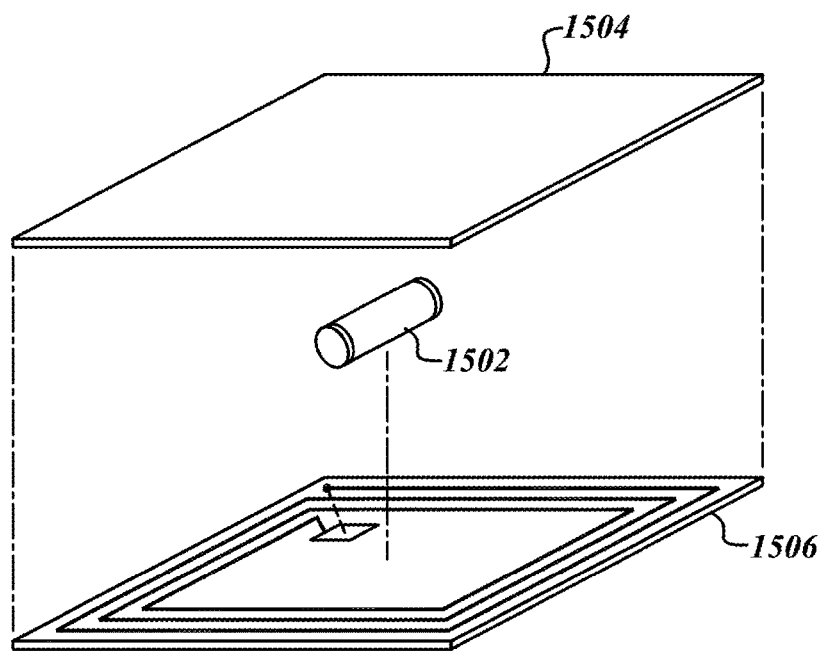
FIG. 15 is an exploded view of an RFID transponder, an LC resonant transponder, and a piece of material, according to at least one illustrated embodiment, the piece of material is attachable to a piece of gauze to retain the LC resonant and optionally the RFID transponder to the piece of gauze.

FIG. 15 shows an assembly comprised of an LC resonant transponder 1502, a piece of material 1504 and optionally an RFID transponder 1506, according to at least one illustrated embodiment. The piece of material 1506 is attachable to a piece of gauze 100*a*, 100*b* (FIGS. 1A-1D, 2A-2C) to attach and retain the LC resonant transponder 1502 to the piece of gauze 100*a*, 100*b*, and optionally to attach and retain the RFID transponder 1506 to the piece of gauze 100*a*, 100*b*. In contrast to various pouches, the LC resonant transponder 1502 is trapped or retained between the piece of material 1504 and either the piece of gauze 100*a*, 100*b* or the RFID transponder 1506.

Figure 16:
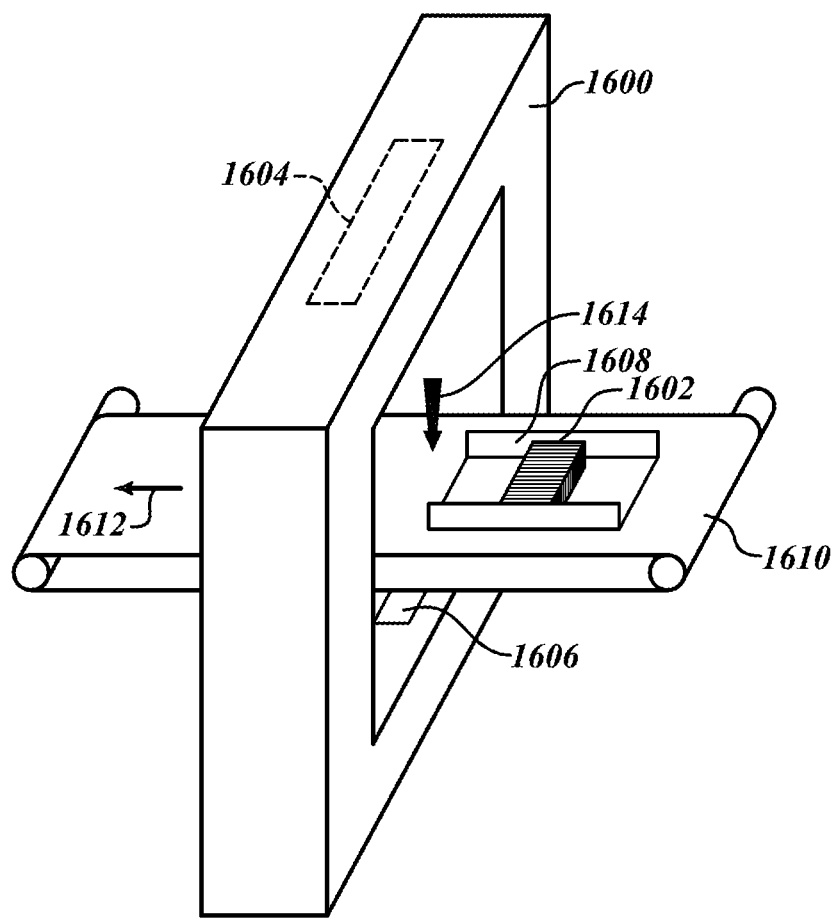
FIG. 16 is an isometric view of an imaging system and a plurality of sponges, the imaging system confirming the count of sponges in a set, packet or package of sponges, according to at least one illustrated embodiment.

FIG. 16 shows an imaging system 1600 and a plurality of sponges 1602, according to at least one illustrated embodiment.

The imaging system 1600 confirms that a count of the total number of sponges in a set, packet or package of sponges 1602 is correct using imaging technology. The imaging system 1600 may employ a variety of imaging technologies, for example X-ray imaging technology. Thus, the imaging system 1600 may include a source (e.g., X-ray source) 1604 and sensor (e.g., X-ray sensor) 1606 (collectively X-ray machine) to illuminate or irradiate the set, packet or package of sponges 1602, and to identify the radio-opaque material in the sensed image data.

The set, packet or package of sponges 1602 may be carried in a carrier 1608. The carrier 1608 may in turn be carried on a conveyor system (e.g. conveyor belt) 1610 to advance (arrow 1612) the set, packet or package of sponges 1602 into a field of the imaging system 1600. Advantageously, the source transmits electromagnetic radiation (e.g., X-rays) through the sponges endwise (e.g., substantially parallel to the major faces of the sponges), as illustrated by arrow 1614. The sensor 1606 may reside relatively below a portion of the conveyor system 1610, to detect X-rays passing through the sponges 1602. The radio-opaque material on each sponge 1602 will absorb or at least attenuate the X-rays that try to pass through, while the gauze will substantially pass all X-ray radiation. Thus, the radio-opaque material will be clearly discernable and/or detectable in imaging data, for example as spaced black marks or dots. The spacing between adjacent sponges, and hence between sets of black marks or dots will typically be highly repetitive and predictable. Knowledge of the expected spacing can increase the certainty of any evaluation. Evaluation is preferably performed autonomously by a processor-based device (e.g., imaging system, computer), although can alternatively be performed manually. Spacing the radio-opaque material relatively inward in each sponge 1602, advantageously increases the spacing between the radio-opaque material of neighboring or adjacent sponges 1602, enhancing the ability to discern one sponge 1602 from the next, thereby increasing the accuracy of counting. The positioning of the transponders relative to the radio-opaque material may also advantageously eliminate noise or interference in the image data.

Figure 17:
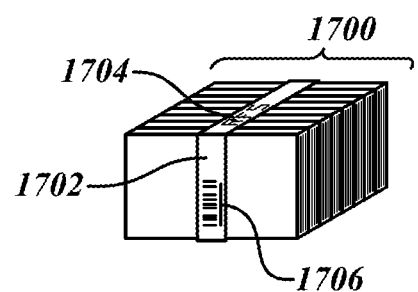
FIG. 17 is an isometric view of a set, packet or package of sponges with a band bearing one or more indications that the total number of sponges in the set, packet or package of sponges has been verified, according to at least one illustrated embodiment.

FIG. 17 shows a set, packet or package of sponges 1700 with a band 1702, according to at least one illustrated embodiment.

The presence of the band 1702 may be indicative that the count of the number of sponges a set, packet or package of sponges 1700 has been checked or verified. The band 1702 may bear one or more indications that the total number of sponges in the set, packet or package of sponges has been checked or verified, and is accurate. For example, the band 1702 may bear a mark or insignia (e.g., trademark) or hologram, collectively 1704, indicative of the accuracy of the count. Additionally or alternatively, the band 1702 may bear a machine-readable symbol (e.g., one-dimensional barcode symbol, two-dimensional matrix code symbol) 1706 indicative of the accuracy of the count. The band may be applied manually or automatically by a machine on confirmation or verification that the count of total sponges in the set, packet or package of sponges 1700 is correct.

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other absorbent materials, other types of transponders, and other interrogation and detection systems. For instance, the transponder device may be used to mark objects anytime detection of the presence of marked objects is desirable in a confined area, not just during surgery. For example, it may be used to make sure marked objects are not left inside a machine (e.g., vehicle, copy machine) after maintenance is performed. In at least some embodiments, the transponder housing may be utilized to mark objects to determine the removal of a marked object from a confined area, such as a cover-all garment from a clean room of a semiconductor fabrication plant. In such an embodiment, an interrogation device, for example, may be placed proximate to a door of the confined area.

In addition, a transponder pouch may be manufactured and distributed for tagging objects without a transponder currently attached or received therein. Advantageously, the pouch can then be used to place a transponder compatible with a particular detection and interrogation system at a subsequent time, including by the end-user.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. Pat. Nos. 8,358,212; 8,710,957; 8,726,911; U.S. Patent Application Publication No. 2010/0108079; U.S. Provisional Patent Application Ser. No. 60/811,376 filed Jun. 6, 2006; U.S. Provisional Patent Application Ser. No. 60/892,208, filed Feb. 28, 2007; U.S. Provisional Patent Application Ser. No. 61/109,142 filed Oct. 28, 2008; U.S. provisional patent application Ser. No. 62/106,052 filed Jan. 21, 2015; and in U.S. provisional patent application Ser. No. 62/138,248 filed Mar. 25, 2015 are incorporated herein by reference, in their entirety. Aspects of the embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure.

What is claimed is:

1. A sponge, comprising:
an elongated strip of gauze longitudinally folded in on itself to form at least four longitudinal panels which overlap with one another, including a first outer panel, a second outer panel and at least two inner panels located interposed between the first outer panel and the second outer panel,
wherein the at least two inner panels include a first inner panel longitudinally adjacent to the first outer panel, and a second inner panel longitudinally adjacent to the second outer panel;
a first radio-opaque material supported on one of the at least two inner panels; and
a second radio-opaque material supported on another of the at least two inner panels, such that the first radio-opaque material and the second radio-opaque material are always supported on differing inner panels.

2. The sponge of claim 1, wherein the first radio-opaque material is a first radio-opaque thread woven into the gauze.

3. The sponge of claim 1, wherein the first radio-opaque material is a first radio-opaque thread attached to a face of the gauze.

4. The sponge of claim 1, wherein the first radio-opaque material is a first radio-opaque thread attached to a face of the first inner panel that faces the first outer panel and the second radio-opaque material is a second radio-opaque thread attached to a face of the second inner panel that faces the second outer panel.

5. The sponge of claim 1 wherein, in a pre-folded configuration, the piece of gauze has a left-most portion and a right-most portion with respect to a centerline that traverses a width of the gauze along a longitudinal length thereof, and in a folded configuration, the left-most portion of the piece of gauze is immediately adjacent the right-most portion of the piece of gauze with respect to a thickness of the sponge.

6. The sponge of claim 1, further comprising:
a transponder attached to the gauze.

* * * * *